(12) United States Patent
Okazoe et al.

(10) Patent No.: US 9,617,379 B2
(45) Date of Patent: Apr. 11, 2017

(54) PRODUCTION METHOD FOR CARBONATE COMPOUND AND METHACRYLATE OR ESTER THEREOF

(71) Applicant: Asahi Glass Company, Limited, Chiyoda-ku (JP)

(72) Inventors: Takashi Okazoe, Tokyo (JP); Masayuki Miyazaki, Tokyo (JP); Kazuya Oharu, Tokyo (JP); Tomoyuki Fujita, Tokyo (JP); Shinji Wada, Tokyo (JP); Koichi Murata, Tokyo (JP); Naoko Shirota, Tokyo (JP)

(73) Assignee: ASAHI GLASS COMPANY, LIMITED, Chiyoda-ku (JP)

( * ) Notice: Subject to any disclaimer, the term of this patent is extended or adjusted under 35 U.S.C. 154(b) by 0 days.

(21) Appl. No.: 15/233,981

(22) Filed: Aug. 11, 2016

(65) Prior Publication Data
US 2016/0347905 A1 Dec. 1, 2016

Related U.S. Application Data

(63) Continuation of application No. PCT/JP2015/053879, filed on Feb. 12, 2015.

(30) Foreign Application Priority Data

Feb. 17, 2014 (JP) ................. 2014-027764

(51) Int. Cl.
| | | |
|---|---|---|
| C08G 63/02 | (2006.01) | |
| C08G 64/00 | (2006.01) | |
| C08G 64/30 | (2006.01) | |
| C07C 29/38 | (2006.01) | |
| C07C 67/00 | (2006.01) | |
| C07C 67/14 | (2006.01) | |
| C07C 67/317 | (2006.01) | |
| C07C 68/00 | (2006.01) | |
| C07C 68/06 | (2006.01) | |
| C07C 45/63 | (2006.01) | |
| C07C 49/16 | (2006.01) | |
| C07C 51/16 | (2006.01) | |
| C07C 51/377 | (2006.01) | |
| C07C 57/04 | (2006.01) | |
| C07C 17/361 | (2006.01) | |
| C08G 64/06 | (2006.01) | |

(52) U.S. Cl.
CPC .......... *C08G 64/307* (2013.01); *C07C 17/361* (2013.01); *C07C 29/38* (2013.01); *C07C 45/63* (2013.01); *C07C 49/16* (2013.01); *C07C 51/16* (2013.01); *C07C 51/377* (2013.01); *C07C 57/04* (2013.01); *C07C 67/00* (2013.01); *C07C 67/14* (2013.01); *C07C 67/317* (2013.01); *C07C 68/00* (2013.01); *C07C 68/06* (2013.01); *C08G 64/00* (2013.01); *C08G 64/06* (2013.01)

(58) Field of Classification Search
CPC .................................................. C08G 64/307
USPC ..... 528/196, 198; 548/124, 219, 221, 330.1; 558/272, 276
See application file for complete search history.

(56) References Cited

U.S. PATENT DOCUMENTS

| | | |
|---|---|---|
| 2,226,645 A | 12/1940 | Thomas et al. |
| 2,462,389 A | 2/1949 | Harrington |
| 2,635,117 A | 4/1953 | Woolf et al. |
| 3,153,008 A | 10/1964 | Fox |
| 2010/0240912 A1 | 9/2010 | Okamoto et al. |
| 2010/0249436 A1 | 9/2010 | Okamoto et al. |

FOREIGN PATENT DOCUMENTS

| | | |
|---|---|---|
| GB | 754295 A | 8/1956 |
| JP | 3-291257 A | 12/1991 |
| JP | 2007-254311 A | 10/2007 |
| WO | WO 2009/072501 A1 | 6/2009 |
| WO | WO 2009/072502 A1 | 6/2009 |
| WO | WO 2010/140572 A1 | 12/2010 |
| WO | WO 2014/024891 A1 | 2/2014 |
| WO | WO 2014/038489 A1 | 3/2014 |
| WO | WO 2014/088029 A1 | 6/2014 |

OTHER PUBLICATIONS

International Search Report issued Apr. 14, 2015 in PCT/JP2015/053879 (with English language translation).

*Primary Examiner* — Terressa Boykin
(74) *Attorney, Agent, or Firm* — Oblon, McClelland, Maier & Neustadt, L.L.P.

(57) ABSTRACT

The present invention relates to a method for producing a carbonate compound and methacrylic acid or an ester thereof, containing a step (a1) of obtaining hexachloroacetone and hydrogen chloride from acetone and chlorine molecule, a step (a2) of obtaining a dialkyl carbonate and chloroform from hexachloroacetone and an alkyl alcohol, a step (b1) of obtaining 1,1,1-trichloro-2-methyl-2-propanol from chloroform and acetone, a step (b2+b3 or b4) of obtaining methacrylic acid or an ester thereof and hydrogen chloride from 1,1,1-trichloro-2-methyl-2-propanol and water or an alcohol, and a step (c1 or c2) of obtaining chlorine molecule by reacting hydrogen chloride with oxygen molecule.

8 Claims, No Drawings

PRODUCTION METHOD FOR CARBONATE COMPOUND AND METHACRYLATE OR ESTER THEREOF

TECHNICAL FIELD

The present invention relates to a method for producing a carbonate compound (a dialkyl carbonate, an aromatic polycarbonate, etc.) and methacrylic acid or an ester thereof.

BACKGROUND ART

Aromatic polycarbonates have been widely used in many fields as engineering plastics excellent in heat resistance, impact resistance, transparency, and the like.

Methacrylic resins obtained by polymerizing methacrylate esters are excellent in transparency and weather resistance and have been widely used as illumination devices, automobile parts, building-related materials, flat display materials, and the like.

As an industrial method for producing aromatic polycarbonates, the following methods (I) and (II) have been known:

(I) a method of causing interfacial polycondensation of bisphenol A with phosgene in the presence of an alkali catalyst; and (II) a method of causing melt-polycondensation of bisphenol A with diphenyl carbonate (Patent Document 1).

According to the method (I), colorless and transparent polycarbonates can be obtained since the reaction proceeds at a low temperature. However, the method (I) has the following problems: toxic phosgene is used; inorganic salts such as sodium chloride produced by the reaction as by-products should be removed by washing; complex processes such as purification of the polymer and recovery of solvents after the reaction become necessary because of using solvents such as methylene chloride; and the like.

On the other hand, in the method (II), it is not necessary to use phosgene. Also, since it is not necessary to use any solvent, the separation of the polycarbonate from the reaction system is easy.

As a method for obtaining diphenyl carbonate to be used in the method (II), for example, the following methods have been known:

(II-1) a method of reacting phosgene with phenol to obtain diphenyl carbonate; and (II-2) a method of obtaining diphenyl carbonate via an ester exchange reaction of a dialkyl carbonate with phenol and a disproportionation reaction (Patent Documents 2, 3).

However, in the method (II-1), there is a problem of using toxic phosgene.

On the other hand, in the method (II-2), it is not necessary to use phosgene.

As a method for obtaining a dialkyl carbonate to be used in the method (II-2), for example, the following methods have been known:

(II-2-1) a method of oxidizing ethylene to form ethylene oxide, reacting carbon dioxide produced as a by-product at that time with the ethylene oxide to obtain ethylene carbonate, and subsequently reacting the ethylene carbonate with an aliphatic alcohol to obtain a dialkyl carbonate and ethylene glycol; and (II-2-2) a method of reacting carbon monoxide with an aliphatic alcohol to obtain a dialkyl carbonate; and (II-2-3) a method of reacting acetone with chlorine molecule to obtain hexachloroacetone and hydrogen chloride and subsequently reacting the hexachloroacetone with an alcohol to obtain a dialkyl carbonate and chloroform (Patent Documents 4, 5).

However, the method (II-2-1) has a limitation that it is realized only at a place where there are facilities for oxidizing ethylene to form ethylene oxide and reacting carbon dioxide produced as a by-product at that time with the ethylene oxide. Also, in the method (II-2-1), the amount of production of the dialkyl carbonate varies depending on the demand for ethylene glycol.

The method (II-2-2) has a problem of using toxic carbon monoxide. Also, the method (II-2-2) has a limitation on reaction conditions and catalyst life.

Chloroform produced as a by-product in the method (II-2-3) can be utilized as a raw material for various fluorine-based materials. However, in the method (II-2-3), as compared with the demand for polycarbonates finally obtained by using the dialkyl carbonate as a raw material, the demand for the fluorine-based materials is small, so that the amount of production of the dialkyl carbonate is limited by the demand for the fluorine-based materials.

As an industrial method for producing a methacrylate ester, the following methods (i) to (v) have been known.

(i) a method of treating acetone cyanohydrin obtained from acetone and hydrogen cyanide with sulfuric acid and subsequently reacting the resultant with an alcohol;

(ii) a method of converting isobutylene or tert-butyl alcohol into methacrylic acid by a two-stage oxidation reaction, and esterifying the methacrylic acid;

(iii) a method of subjecting tert-butyl alcohol to vapor-phase oxidation to form methacrolein and subsequently obtaining a methacrylate ester through oxidative esterification by a liquid-phase catalytic reaction of the methacrolein in methanol;

(iv) a method of subjecting acetone cyanohydrin obtained from acetone and hydrogen cyanide to a hydration reaction to form α-hydroxyisobutyramide, converting α-hydroxyisobutyramide into methyl α-hydroxyisobutyrate by an amide-ester exchange reaction with methyl formate, and subsequently obtaining methyl methacrylate by a dehydration reaction of the methyl α-hydroxyisobutyrate; and (v) a method of obtaining methyl propanoate from ethylene, methanol, and carbon monoxide and subsequently subjecting methyl propanoate to a vapor-phase condensation with formaldehyde to obtain methyl methacrylate.

However, the method (i) has the following problems: toxic hydrogen cyanide is used; hydrogen cyanide is available mainly as a by-product of acrylonitrile but there is a limitation on its availability; it is necessary to treat waste acid involved in the use of sulfuric acid; and it is possible to react the waste acid with ammonia to form ammonium sulfate but it takes a cost; and the like.

The method (ii) has a limitation on availability of isobutylene and tert-butyl alcohol.

The method (iii) has a limitation on availability of tert-butyl alcohol.

Since the method (iv) is a multi-stage process, it consumes large energy. Moreover, there is a limitation that it is realized only at a place where there are facilities capable of producing the formic acid derivative.

The method (v) has a problem of using toxic carbon monoxide. Moreover, the method (v) has a limitation of low conversion rate and catalyst life.

PRIOR ART DOCUMENTS

Patent Documents

Patent Document 1: U.S. Pat. No. 3,153,008
Patent Document 2: JP-A-H03-291257
Patent Document 3: JP-A-2007-254311
Patent Document 4: WO 2009/072501
Patent Document 5: WO 2009/072502

SUMMARY OF THE INVENTION

Problems that the Invention is to Solve

The present invention provides a method for producing a carbonate compound and methacrylic acid or an ester thereof, which method can produce the carbonate compound without using highly toxic gases such as phosgene and carbon monoxide, can produce methacrylic acid or ester thereof without using highly toxic gases such as hydrogen cyanide and carbon monoxide, has no limitation on raw material availability, can effectively utilize by-products, and has no limitation on the amount of production depending on the demand for a by-product.

Means for Solving the Problems

A first aspect of the method for producing a carbonate compound and methacrylic acid or an ester thereof according to the present invention is a method containing:

(a1) a step of reacting acetone with chlorine molecule to obtain hexachloroacetone and hydrogen chloride, (a2) a step of reacting the hexachloroacetone obtained in the step (a1) with an alkyl alcohol having a carbon number of from 1 to 10 to obtain a dialkyl carbonate and chloroform, (b1) a step of reacting chloroform with acetone to obtain 1,1,1-trichloro-2-methyl-2-propanol, (b2) a step of reacting the 1,1,1-trichloro-2-methyl-2-propanol obtained in the step (b1) with water or an alcohol that has a carbon number of from 1 to 10 in which a part or all of hydrogen atoms bonded to carbon atoms may be replaced by halogen atom(s) and/or deuterium atom(s), to obtain 2-chloro-2-methylpropanoic acid or an ester thereof and hydrogen chloride, (b3) a step of obtaining methacrylic acid or an ester thereof and hydrogen chloride from the 2-chloro-2-methylpropanoic acid or the ester thereof obtained in the step (b2), and (c1) a step of reacting the hydrogen chloride obtained in the step (a1), the step (b2), and the step (b3) with oxygen molecule to obtain chlorine molecule, in which the step (b2) contains reacting the 1,1,1-trichloro-2-methyl-2-propanol obtained in the step (b1) in the presence of a Lewis acid catalyst at a temperature lower than the boiling point of the 1,1,1-trichloro-2-methyl-2-propanol, after the chloroform is obtained in the step (a2), the chloroform obtained in the step (a2) is used as at least a part of the chloroform in the step (b1), and after the chlorine molecule is obtained in the step (c1), the chlorine molecule obtained in the step (c1) is used as at least a part of the chlorine molecule in the step (a1).

The step (b2) may be a step containing reacting the 1,1,1-trichloro-2-methyl-2-propanol obtained in the step (b1) in the presence of the Lewis acid catalyst at the temperature lower than the boiling point of the 1,1,1-trichloro-2-methyl-2-propanol and further reacting the resulting one with the water or the alcohol that has a carbon number of from 1 to 10 in which a part or all of hydrogen atoms bonded to carbon atoms may be replaced by halogen atom(s) and/or deuterium atom(s), to obtain the 2-chloro-2-methylpropanoic acid or the ester thereof and the hydrogen chloride.

Also, the step (b2) may be a step containing reacting the 1,1,1-trichloro-2-methyl-2-propanol obtained in the step (b1) with the water or the alcohol that has a carbon number of from 1 to 10 in which a part or all of hydrogen atoms bonded to carbon atoms may be replaced by halogen atom(s) and/or deuterium atom(s), in the presence of the Lewis acid catalyst at the temperature lower than the boiling point of the 1,1,1-trichloro-2-methyl-2-propanol to obtain the 2-chloro-2-methylpropanoic acid or the ester thereof and the hydrogen chloride.

A second aspect of the method for producing a carbonate compound and methacrylic acid or an ester thereof according to the present invention is a method containing:

(a1) a step of reacting acetone with chlorine molecule to obtain hexachloroacetone and hydrogen chloride, (a2) a step of reacting the hexachloroacetone obtained in the step (a1) with an alkyl alcohol having a carbon number of from 1 to 10 to obtain a dialkyl carbonate and chloroform, (b1) a step of reacting chloroform with acetone to obtain 1,1,1-trichloro-2-methyl-2-propanol, (b4) a step of reacting the 1,1,1-trichloro-2-methyl-2-propanol obtained in the step (b1) with water or an alcohol that has a carbon number of from 1 to 10 in which a part or all of hydrogen atoms bonded to carbon atoms may be replaced by halogen atom(s) and/or deuterium atom(s), in the presence of a Lewis acid catalyst at a temperature equal to or higher than the boiling point of the 1,1,1-trichloro-2-methyl-2-propanol to obtain methacrylic acid or an ester thereof and hydrogen chloride, and (c2) a step of reacting the hydrogen chloride obtained in the step (a1) and the step (b4) with oxygen molecule to obtain chlorine molecule, in which, after the chloroform is obtained in the step (a2), the chloroform obtained in the step (a2) is used as at least a part of the chloroform in the step (b1), and after the chlorine molecule is obtained in the step (c2), the chlorine molecule obtained in the step (c2) is used as at least a part of the chlorine molecule in the step (a1).

A third aspect of the method for producing a carbonate compound and methacrylic acid or an ester thereof according to the present invention is a method further containing:

in addition to the first aspect or the second aspect, (a3) a step of reacting the dialkyl carbonate obtained in the step (a2) with phenol to obtain diphenyl carbonate and an alkyl alcohol having a carbon number of from 1 to 10, and (a4) a step of reacting the diphenyl carbonate obtained in the step (a3) with bisphenol A to obtain an aromatic polycarbonate and phenol in which, after the alkyl alcohol having a carbon number of from 1 to 10 is obtained in the step (a3), the alkyl alcohol having a carbon number of from 1 to 10 obtained in the step (a3) is used as at least a part of the alkyl alcohol having a carbon number of from 1 to 10 in the step (a2), and after the phenol is obtained in the step (a4), the phenol obtained in the step (a4) is used as at least a part of the phenol in the step (a3).

Advantage of the Invention

The method for producing a carbonate compound and methacrylic acid or an ester thereof according to the present invention can produce a carbonate compound without using highly toxic gases such as phosgene and carbon monoxide, can produce methacrylic acid or an ester thereof without using highly toxic gases such as hydrogen cyanide and carbon monoxide, has no limitation on raw material availability, can effectively utilize by-products, and has no limitation on the amount of production depending on the demand for a by-product.

MODES FOR CARRYING OUT THE INVENTION

The following definitions of terms are applied to the present Description and Claims.

The "carbonate compound" means a compound having a carbonate bond (—O—C(=O)—O—) and includes a polycarbonate.

The "Lewis acid" means an electron pair acceptor and is a concept including a Brønsted acid.

The "Brønsted acid" means a proton donor.

The "solid acid" means a substance which is a solid and shows acidity.

The "batch-wise mode" means a reaction mode where raw materials and a catalyst are placed in an arbitrary reaction vessel and, after they are reacted at a predetermined temperature for a certain time, a reaction product is taken out at a time.

The "continuous mode" means a reaction mode where raw materials are continuously supplied to a catalyst layer at a constant rate under an arbitrary atmosphere, allowed to stay for a certain time in the catalyst layer, and reacted to produce a reaction product continuously.

The "boiling point" is a boiling point at normal pressure (1 atm, 101325 Pa).

The method for producing a carbonate compound and methacrylic acid or an ester thereof according to the present invention is classified into a method (α) and a method (β) to be mentioned below, depending on the difference in the method of obtaining methacrylic acid or an ester thereof from 1,1,1-trichloro-2-methyl-2-propanol obtained in the step (b1).

The following will describe each of the method (α) and the method (β).

<Method (α)>

The method (α) is a method containing:

(a1) a step of reacting acetone with chlorine molecule to obtain hexachloroacetone and hydrogen chloride, (a2) a step of reacting hexachloroacetone obtained in the step (a1) with an alkyl alcohol having a carbon number of from 1 to 10 to obtain a dialkyl carbonate and chloroform, (a3) if necessary, a step of reacting the dialkyl carbonate obtained in the step (a2) with phenol to obtain diphenyl carbonate and an alkyl alcohol having a carbon number of from 1 to 10 and (a4) if necessary, a step of reacting the diphenyl carbonate obtained in the step (a3) with bisphenol A to obtain an aromatic polycarbonate and phenol, (b1) a step of reacting chloroform with acetone to obtain 1,1,1-trichloro-2-methyl-2-propanol, (b2) a step of reacting the 1,1,1-trichloro-2-methyl-2-propanol obtained in the step (b1) with water or an alcohol having a carbon number of from 1 to 10 in which a part or all of hydrogen atoms bonded to carbon atoms may be replaced by halogen atom(s) and/or deuterium atom(s), to obtain 2-chloro-2-methylpropanoic acid or an ester thereof and hydrogen chloride, (b3) a step of obtaining methacrylic acid or an ester thereof and hydrogen chloride from 2-chloro-2-methylpropanoic acid or the ester thereof obtained in the step (b2), and (c1) a step of oxidizing the hydrogen chloride obtained in the step (a1), the step (b2) and the step (b3) with oxygen to obtain a chlorine molecule, in which the step (b2) contains reacting the 1,1,1-trichloro-2-methyl-2-propanol obtained in the step (b1) in the presence of a Lewis acid catalyst at a temperature lower than the boiling point of 1,1,1-trichloro-2-methyl-2-propanol, after chloroform is obtained in the step (a2), the chloroform obtained in the step (a2) is used as at least a part of chloroform in the step (b1), after the alkyl alcohol having a carbon number of from 1 to 10 is obtained in the step (a3), the alkyl alcohol having a carbon number of from 1 to 10 obtained in the step (a3) is used as at least a part of the alkyl alcohol having a carbon number of from 1 to 10 in the step (a2), after phenol is obtained in the step (a4), the phenol obtained in the step (a4) is used as at least a part of phenol in the step (a3), and after chlorine molecule is obtained in the step (c1), the chlorine molecule obtained in the step (c1) is used as at least a part of chlorine molecule in the step (a1).

The following shows a reaction scheme in the method (α).

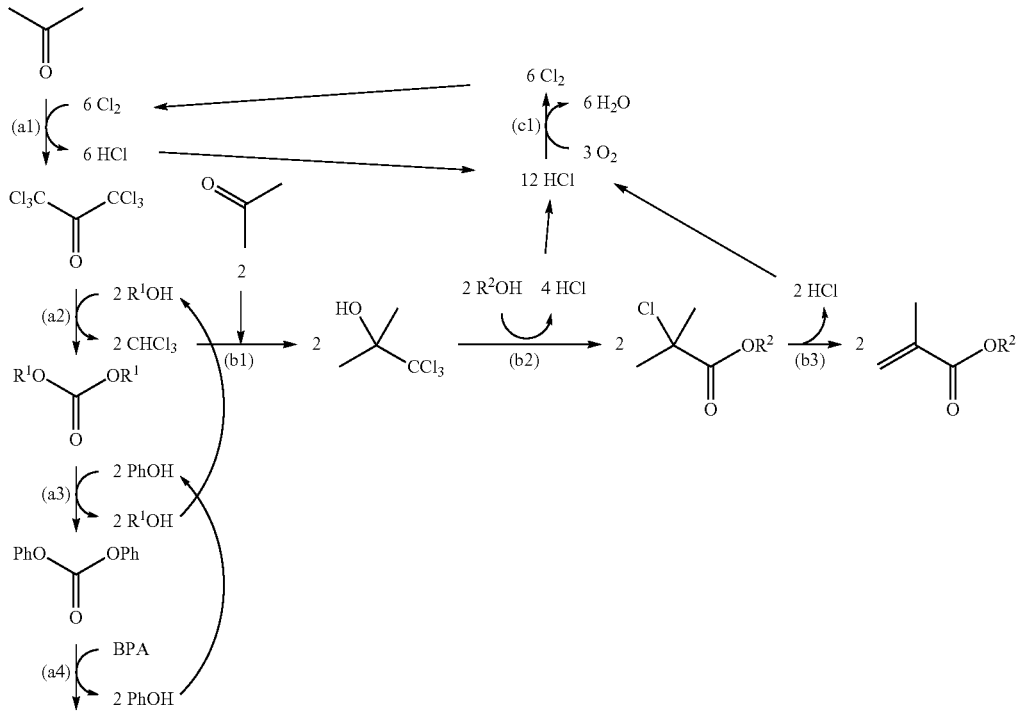

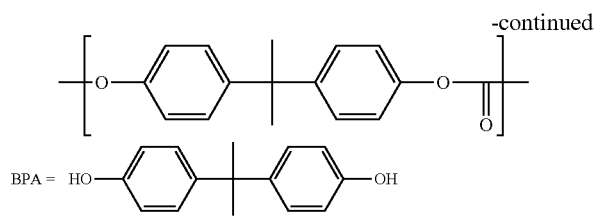

In the reaction scheme, $R^1$ is an alkyl group having a carbon number of from 1 to 10, $R^2$ is a hydrogen atom, a hydrocarbon group having a carbon number of from 1 to 10, or a group in which a part or all of hydrogen atoms bonded to the carbon atom(s) of the hydrocarbon group having a carbon number of from 1 to 10 are replaced by halogen atom(s) and/or deuterium atom(s), and Ph is a phenyl group.

As shown in the reaction scheme, in the case where the reaction ideally proceeds in 100% yield in each step in the method (α), the substance discharged into the outside of the system is water alone other than the objective products (a carbonate compound and methacrylic acid or an ester thereof). Also, in the case where the reaction ideally proceeds in 100% yield in each step in the method (α), since chlorine (hydrogen chloride and chloroform), $R^1OH$ and PhOH are all re-used in the system, it is not necessary to replenish a chlorine source, $R^1OH$ and PhOH into the system. Furthermore, in the case where the reaction ideally proceeds in 100% yield in each step in the method (α), the objective products (a carbonate compound and methacrylic acid or an ester thereof) can be obtained only by supplying acetone, bisphenol A, $R^2OH$, and oxygen molecule.

(Step (a1))

The method of reacting acetone with chlorine molecule to obtain hexachloroacetone and hydrogen chloride includes the method described in Japanese Patent No. 1329825 and the method described in Japanese Patent No. 1354304. The resulting hexachloroacetone and hydrogen chloride may be purified by a known method.

In the initial stage of the reaction of the step (a1), chlorine molecule is supplied from outside of the system and subjected to a reaction with acetone. After chlorine molecule begins to be obtained in the step (c1) to be mentioned below, the chlorine molecule obtained in the step (c1) is supplied to the step (a1) and subjected to a reaction with acetone. In the case where the amount of the chlorine molecule obtained in the step (c1) is insufficient, chlorine molecule may be replenished from outside of the system and subjected to a reaction with acetone.

(Step (a2))

The method of reacting hexachloroacetone with an alkyl alcohol having a carbon number of from 1 to 10 to obtain a dialkyl carbonate and chloroform includes the method described in Patent Document 4. That is, in the presence of a catalyst for carbonate compound synthesis, hexachloroacetone is subjected to a reaction with an alkyl alcohol having a carbon number of from 1 to 10 to obtain a dialkyl carbonate and chloroform. The resulting dialkyl carbonate and chloroform may be purified by known methods.

In the initial stage of the reaction of the step (a2), the alkyl alcohol having a carbon number of from 1 to 10 is supplied from outside of the system and subjected to a reaction with hexachloroacetone. After the alkyl alcohol having a carbon number of from 1 to 10 begins to be obtain in the step (a3) to be mentioned later, the alkyl alcohol having a carbon number of from 1 to 10 obtained in the step (a3) is supplied to the step (a2) and subjected to a reaction with hexachloroacetone. In the case where the amount of the alkyl alcohol having a carbon number of from 1 to 10 obtained in the step (a3) is insufficient, the alkyl alcohol having a carbon number of from 1 to 10 may be replenished from outside of the system and subjected to a reaction with hexachloroacetone.

As the alkyl alcohol, in view of versatility for industrial use, alkyl alcohols having a carbon number of from 1 to 10 are used. Incidentally, the alkyl alcohol having a carbon number of from 1 to 10 may have an ethereal oxygen atom. In view of usefulness of the dialkyl carbonate, an alkyl alcohol having a carbon number of from 1 to 4 is preferred. Specifically, methanol, ethanol, n-propyl alcohol, i-propyl alcohol, n-butyl alcohol, tert-butyl alcohol, and 3-oxa-n-butyl alcohol are more preferred.

The catalyst for carbonate compound synthesis includes basic compounds (hydroxides of an alkali metal or an alkaline earth metal, carbonate salts or hydrogen carbonate salts of an alkali metal or an alkaline earth metal, etc.), phase transfer catalysts (quaternary ammonium salts, quaternary phosphonium salts, quaternary arsonium salts, sulfonium salts, etc.), halide salts of an alkali metal or an alkaline earth metal, ammonium halide salts, quaternary ammonium halide salts, and ion-exchange resins; compounds or oxide of one or more metals selected from the group consisting of tin, titanium, aluminum, tungsten, molybdenum, zirconium, and zinc, and the like.

(Step (a3))

The method of reacting a dialkyl carbonate with phenol to obtain diphenyl carbonate and an alkyl alcohol having a carbon number of from 1 to 10 includes the methods described in Patent Documents 2 and 3. That is, in the presence of a known ester exchange catalyst, a dialkyl carbonate and phenol are subjected to an ester exchange reaction to obtain an alkyl phenyl carbonate and an alkyl alcohol having a carbon number of from 1 to 10 and subsequently, the alkyl phenyl carbonate is subjected to a disproportionation reaction to obtain diphenyl carbonate and a dialkyl carbonate. The resulting diphenyl carbonate and alkyl alcohol having a carbon number of from 1 to 10 may be purified by known methods.

In the initial stage of the reaction of the step (a3), phenol is supplied from outside of the system and subjected to a reaction with a dialkyl carbonate. After phenol begins to be obtained in the step (a4) to be mentioned later, the phenol obtained in the step (a4) is supplied to the step (a3) and subjected to a reaction with a dialkyl carbonate. In the case where the amount of the phenol obtained in the step (a4) is insufficient, phenol may be replenished from outside of the system and subjected to a reaction with a dialkyl carbonate.

(Step (a4))

The method of reacting diphenyl carbonate with bisphenol A to obtain an aromatic polycarbonate and phenol includes the method described in Patent Document 1. That is, in the presence of a known catalyst for polycarbonate synthesis, diphenyl carbonate and bisphenol A are subjected to melt-polycondensation to obtain an aromatic polycarbonate and phenol. The resulting aromatic polycarbonate and phenol may be purified by known methods.

(Step (b1))

The method of reacting chloroform with acetone to obtain 1,1,1-trichloro-2-methyl-2-propanol includes the methods described in JP-A-S49-82611, U.S. Pat. No. 2,462,389, and J. Org. Chem., vol. 65, 2000, pp. 7211-7212. That is, in the presence of a basic compound, chloroform and acetone are subjected to a reaction with each other to obtain 1,1,1-trichloro-2-methyl-2-propanol. The resulting 1,1,1-trichloro-2-methyl-2-propanol may be purified by a known method.

In the step (b1), after chloroform begins to be obtained in the step (a2), the chloroform obtained in the step (a2) may be supplied to the step (b1) and subjected to a reaction with acetone; or chloroform is supplied from outside of the system in the initial stage of the reaction and subjected to a reaction with acetone and, after chloroform begins to be obtained in the step (a2), the chloroform obtained in the step (a2) may be supplied to the step (b1) and subjected to a reaction with acetone. In the case where the amount of the chloroform obtained in the step (a2) is insufficient, chloroform may be replenished from outside of the system and subjected to a reaction with acetone.

(Step (b2))

A 1,1,1-trichloro-2-methyl-2-propanol is subjected to a reaction with water or an alcohol having a carbon number of from 1 to 10 in which a part or all of hydrogen atoms bonded to carbon atoms may be replaced by halogen atom(s) and/or deuterium atom(s), to obtain 2-chloro-2-methylpropanoic acid or an ester thereof and hydrogen chloride. This step includes subjecting 1,1,1-trichloro-2-methyl-2-propanol obtained in the step (b1) to a reaction in the presence of a Lewis acid catalyst at a temperature lower than the boiling point of 1,1,1-trichloro-2-methyl-2-propanol. The resulting 2-chloro-2-methylpropanoic acid or an ester thereof may be purified by a known method.

In the step (b2), specifically, a first-stage chlorine transfer/hydrogen chloride elimination reaction and a second-stage hydrogen chloride elimination reaction as described below proceed.

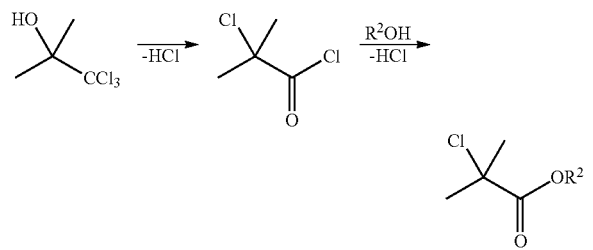

Alcohol:

Examples of the alcohol include methanol, ethanol, n-propyl alcohol, i-propyl alcohol, n-butyl alcohol, i-butyl alcohol, tert-butyl alcohol, pentanol, hexanol, cyclohexanol, heptanol, 2-ethylhexanol, phenol, benzyl alcohol, and those in which at least a part of hydrogen atoms bonded to carbon atoms of these alcohols are replaced by halogen atom(s) and/or deuterium atom(s).

Examples of the halogen-substituted alcohol include 2,2,2-trichloroethanol, 2,2,3,3-tetrafluoropropanol, 1,1,1,3,3,3-hexafluoro-2-propanol, and fluoroalkyl alcohols represented by $C_pF_{2p+1}(CH_2)_qOH$ (where p is an integer of 1 to 8 and q is an integer of 1 to 3, satisfying p+q≤10.).

Specific examples of $C_pF_{2p+1}(CH_2)_qOH$ include $CF_3CH_2OH$, $CF_3CF_2CH_2OH$, $CF_3CF_2CF_2CH_2OH$, $CF_3(CF_2)_3CH_2OH$, $CF_3(CF_2)_5CH_2OH$, $CF_3CF_2CH_2CH_2OH$, $CF_3(CF_2)_3CH_2CH_2OH$, $CF_3(CF_2)_5CH_2CH_2OH$, $CF_3(CF_2)_7CH_2CH_2OH$, $CF_3CF_2(CH_2)_3OH$, $CF_3(CF_2)_3(CH_2)_3OH$, and $CF_3(CF_2)_5(CH_2)_3OH$.

Examples of the deuterium-substituted alcohols include methanol and ethanol in which at least a part of hydrogen atoms bonded to carbon atoms are replaced by deuterium atom(s).

As the alcohol, methanol, ethanol, and/or those in which at least a part of hydrogen atoms bonded to their carbon atoms are replaced by halogen atom(s) and/or deuterium atom(s) are preferred, and methanol is more preferred.

The amount of water or the alcohol to be used is preferably from 0.5 mol to 20 mol, more preferably from 1 mol to 10 mol, and further preferably from 1 mol to 5 mol relative to 1 mol of 1,1,1-trichloro-2-methyl-2-propanol. In the case where the amount of water or the alcohol to be used is equal to or more than the lower limit, a sufficient conversion rate can be obtained. In the case where the amount of water or the alcohol to be used is equal to or less than the upper limit, volume efficiency increases and production efficiency is improved.

Water or the alcohol may be present together with 1,1,1-trichloro-2-methyl-2-propanol from the beginning of the step (b2), or may be added to the reaction system in the course of the step (b2). In view of the yields of 2-chloro-2-methylpropanoic acid or an ester thereof, it is preferred to add water or the alcohol to the reaction system in the course of the step (b2).

Water or the alcohol may be used as a mixture with a solvent or diluent gas to be mentioned later.

Lewis Acid Catalyst:

Examples of the Lewis acid catalyst include one kind or a mixture of two or more kinds selected from compounds represented by the following formula (1) (provided that water is excluded):

$$M_nY_m \qquad (1)$$

in the formula (1),

M is a hydrogen ion or a cation of a metal or a semi-metal selected from the group consisting of Groups 2 and 4 to 14 elements of the periodic table;

Y is an anion selected from the group consisting of halide ions, a sulfate ion, a nitrate ion, a carbonate ion, a hydrogen carbonate ion, sulfide ions, oxide ions, a hydroxide ion, alkoxide ions, a phosphate ion, an acetate ion, and a perchlorate ion; and n and m are numerals satisfying the equation: Valence number of M×n=Valence number of Y×m.

Preferred examples of M include a hydrogen ion or a cation of a metal or a semi-metal selected from the group consisting of boron, magnesium, aluminum, calcium, titanium, vanadium, chromium, manganese, iron, cobalt, nickel, copper, zinc, gallium, germanium, strontium, zirconium, niobium, molybdenum, ruthenium, rhodium, palladium, silver, cadmium, indium, tin, antimony, barium, hafnium, tantalum, tungsten, rhenium, osmium, iridium, platinum, gold, mercury, thallium, and lead. A cation of a metal selected from iron, zinc and copper is further preferred.

Preferred examples of Y include a halide ion, an oxide ion and a sulfide ion. A fluoride ion, a chloride ion or a bromide ion is more preferred.

Specific examples of $M_nY_m$ include boron trichloride, iron chloride, copper chloride, zinc chloride, tin chloride, lead chloride, boron trifluoride, iron fluoride, copper fluoride, zinc fluoride, tin fluoride, lead fluoride, iron bromide, copper bromide, zinc bromide, tin bromide, lead bromide, iron oxide, copper oxide, zinc oxide, tin oxide, lead oxide, iron sulfide, copper sulfide, zinc sulfide, tin sulfide, lead sulfide, and the like.

Other examples of the Lewis acid catalyst include solid acids (activated clay, acid clay, zeolites, heteropoly acids, ion exchange resins, etc.).

Activated clay is one obtained by treating naturally occurring acid clay (montmorillonite-based clay) with a mineral acid such as sulfuric acid, and is a compound having a porous structure. Activated clay contains silicon dioxide, aluminum oxide, iron oxide, calcium oxide, magnesium oxide, and the like as components thereof.

A zeolite has a structure in which a part of the silicon atoms of the substance having silicon dioxide as a basic skeleton is replaced by aluminum atom(s). Specifically, zeolites are defined by the International Zeolite Association (IZA), and there may be mentioned those containing at least oxygen, aluminum and phosphorus as atoms constituting the skeleton structure, those containing at least oxygen, aluminum and silicon as atoms constituting the skeleton structure, and the like.

Heteropoly acids include a complex oxide acid composed of a composite of two or more different oxides, and one in which a part or all of protons thereof are replaced by another cation(s). The heteropoly acid is composed of, for example, an oxyacid ion of an element such as phosphorus, arsenic, tin, silicon, titanium, or zirconium (e.g., phosphoric acid or silicic acid) and an oxyacid ion of another element such as molybdenum, tungsten, vanadium, niobium, or tantalum (e.g., vanadic acid, molybdic acid, tungstic acid), and there are various heteropoly acids resulting from combinations thereof.

Examples of the element of the oxyacid constituting the heteropoly acid include copper, beryllium, boron, aluminum, carbon, silicon, germanium, tin, titanium, zirconium, cerium, thorium, nitrogen, phosphorus, arsenic, antimony, vanadium, niobium, tantalum, chromium, molybdenum, tungsten, uranium, selenium, tellurium, manganese, iodine, iron, cobalt, nickel, rhodium, osmium, iridium, platinum, and the like.

An ion exchange resin is a resin having a carbon fluoride-based polymer, a hydrocarbon-based polymer or the like as a skeleton and having an ion exchange group introduced therein. Examples of the ion exchange group include a cation exchange group such as a sulfonic acid group, a carboxyl group and a phosphoric acid group. The ion exchange resin is particularly preferably an ion exchange resin in which a sulfonic acid group is introduced as an ion exchange group into a perfluorocarbon skeleton having chemical resistance. For example, Flemion manufactured by Asahi Glass Co., Ltd., Nafion manufactured by DuPont, and the like may be mentioned.

The Lewis acid catalyst may be supported on a carrier.

Examples of the kind of the carrier in the case of performing the reaction in a continuous mode include oxides of a metal or a semi-metal and salts thereof, inorganic carbon, and the like. Specifically, silica, alumina, titania, zirconia, zeolites, activated carbon, and the like may be mentioned.

The kind of the carrier in the case of performing the reaction in a batch-wise mode is the same as in the continuous mode. Specifically, silica, alumina, titania, zirconia, and the like may be mentioned.

In the case where the carrier is a Lewis acid, the carrier may also function as a Lewis acid catalyst.

The amount of the catalyst to be used is preferably from 0.001 mol to 1 mol, more preferably from 0.01 mol to 0.2 mol, and further preferably from 0.02 mol to 0.1 mol relative to 1 mol of 1,1,1-trichloro-2-methyl-2-propanol in the reactor in the batch-wise mode and also relative to 1 mol of 1,1,1-trichloro-2-methyl-2-propanol stayed in the reactor in the continuous mode. In the case where the amount of the catalyst to be used is equal to or more than the lower limit value, the production efficiency is improved. In the case where the amount of the catalyst to be used is equal to or less than the upper limit, the volume efficiency is improved.

Solvent or Diluent Gas:

In view of handling of raw materials and control of the heat of reaction, a compound or a gas which does not chemically react with the raw materials and reaction products may be used as a solvent or diluent gas.

Examples of the solvent include pentane, hexane, heptane, petroleum ether, dimethyl ether, diethyl ether, tetrahydrofuran, 1,2-dimethoxyethane, dichloromethane, chloroform, carbon tetrachloride, dichloroethane, acetic acid, benzoic acid, acetic anhydride, ethyl acetate, acetone, 2-butanone, acetonitrile, dimethylformamide, dimethylacetamide, dimethyl sulfoxide, benzene, toluene, chlorobenzene, dichlorobenzene, benzonitrile, nitromethane, nitrobenzene, and mixtures thereof.

Examples of the diluent gas include nitrogen, helium, argon, and mixtures thereof. In view of easy availability and inexpensiveness, nitrogen is preferred.

The amount of the solvent or diluent gas is preferably such an amount that the concentration of 1,1,1-trichloro-2-methyl-2-propanol becomes 5% by mass or more and is more preferably such an amount that the concentration becomes 10% by mass or more. In the case where the concentration of 1,1,1-trichloro-2-methyl-2-propanol is the lower limit or higher, 2-chloro-2-methylpropanoic acid or an ester thereof can be efficiently obtained.

Reaction Mode:

The reaction mode may be a batch-wise mode or a continuous mode.

In the case where the reaction is carried out in a continuous mode, a space velocity is preferably 1 to 500,000 (/hr), more preferably 100 to 50,000 (/hr), and most preferably 100 to 10,000 (/hr).

The space velocity is a mass hourly space velocity per catalyst mass and is a value obtained by dividing the flow rate (kg/hr) of 1,1,1-trichloro-2-methyl-2-propanol by the weight (kg) of the catalyst including the carrier and the like. Incidentally, the inverse of the space velocity is referred to as contact time or residence time.

Reaction Temperature:

The reaction temperature is lower than the boiling point of 1,1,1-trichloro-2-methyl-2-propanol, preferably 0° C. or higher and lower than the boiling point of 1,1,1-trichloro-2-methyl-2-propanol, and more preferably 50° C. or higher and lower than the boiling point of 1,1,1-trichloro-2-methyl-2-propanol. In the case where the reaction temperature is equal to or higher than the lower limit, 2-chloro-2-methylpropanoic acid or an ester thereof can be efficiently obtained. In the case where the reaction temperature is equal to or lower than the upper limit, the reaction proceeds in the liquid phase and it is easy to control the reaction.

The boiling point of 1,1,1-trichloro-2-methyl-2-propanol is 169° C. (167° C. in some literature) and the boiling point of 1,1,1-trichloro-2-methyl-2-propanol 0.5 hydrate is from 173° C. to 175° C.

Reaction Pressure:

The reaction pressure is preferably adjusted as appropriate depending on the vapor pressures of 1,1,1-trichloro-2-methyl-2-propanol, solvent and the other gases, and the reaction may be carried out under pressure or under reduced pressure. The pressure is preferably from 0 MPa to 10 MPa, more preferably from 0.05 MPa to 2 MPa, and further preferably from 0.1 MPa to 1 MPa in absolute pressure.

Reaction Time:

The reaction time is appropriately set depending on various conditions including catalyst and temperature.

In the case where the reaction is carried out in a batch-wise mode, the reaction time is preferably from 10 minutes to 12 hours, and more preferably from 30 minutes to 3 hours.

In the case where the reaction is carried out in a continuous mode, the reaction time is preferably from 0.1 second to 60 minutes, and more preferably from 0.5 second to 30 minutes. In the case of the continuous mode, the reaction time is also referred to as contact time or residence time.

While the reaction is allowed to proceed, a part of the crude reaction liquid may be collected and subjected to a measurement of the concentration of the reaction product by gas chromatography or the like. The amount of the reaction product can be surmised from the concentration and the reaction may be finished at the time when a desirable amount of the reaction product is formed.

Reaction Apparatus:

In the step (b2), since hydrogen chloride that is a strong acid is formed as a by-product, the reaction apparatus is preferably one that is durable to strong acids.

In the reaction apparatus, as a material of a portion that comes into contact with the strong acids, for example, there may be mentioned iron, chromium and nickel, alloys mainly composed of them, quartz, glass, glass-lining, fluororesins (an ethylene-tetrafluoroethylene copolymer, etc.), fluororesin lining, and the like. In view of corrosion resistance, nickel-chromium alloys (Hastelloy, Inconel, Carpenter, etc.), glass, and fluororesins are preferred.

(Step (b3))

The method of obtaining methacrylic acid or an ester thereof and hydrogen chloride from 2-chloro-2-methylpropanoic acid or an ester thereof includes a method by heating, a method by a catalytic reaction, and a method by irradiating light, ultrasound, or microwave.

Catalyst:

Examples of the catalyst include silica, activated carbon, metal oxides such as alumina and zeolites, and the like.

Phase in which Reaction is Carried Out:

In the case of the method by heating, the phase in which the reaction is carried out is preferably a vapor phase.

In the case of the method by a catalytic reaction, the phase in which the reaction is carried may be a liquid phase or a vapor phase. In either case of the liquid phase and the vapor phase, in view of handling of the raw materials and control of the heat of reaction, a compound or a gas which does not chemically react with the raw materials and reaction products may be used as a solvent or diluent gas. As the solvent or the diluent gas, those exemplified in Step (b2) may be mentioned.

Reaction Mode:

The reaction mode may be a batch-wise mode or a continuous mode. In the case of the method by heating, the reaction mode is preferably the continuous mode.

Reaction Temperature:

In the case of the method by heating, the reaction temperature is preferably from 450° C. to 600° C., and more preferably from 520° C. to 550° C.

In the case of the method by the catalytic reaction, the reaction temperature is preferably from 150° C. to 600° C., and more preferably from 200° C. to 350° C.

In the case where the reaction temperature is equal to or higher than the lower limit, methacrylic acid or an ester thereof can be efficiently obtained. In the case where the reaction temperature is equal to or lower than the upper limit, the decomposition of the raw materials and the products and an increase of side reactions can be suppressed.

Reaction Pressure:

The reaction pressure is preferably adjusted as appropriate depending on the vapor pressures of 2-chloro-2-methylpropanoic acid or an ester thereof, solvent and the other gases, and the reaction may be carried out under pressure or under reduced pressure. The pressure is preferably from 0 MPa to 10 MPa, more preferably from 0.05 MPa to 2 MPa, and further preferably from 0.1 MPa to 1 MPa in absolute pressure.

Reaction Apparatus:

The step (b3) may be carried out in a reaction apparatus different from that in the step (b2) or may be carried out the same reaction apparatus.

Since hydrogen chloride that is a strong acid is formed as a by-product in the step (b3), the reaction apparatus is preferably one that is durable to strong acids.

In the reaction apparatus, as a material of a portion that comes into contact with the strong acids, there may be mentioned mild steel, stainless steel, nickel, Inconel, Hastelloy, glass, fluororesin lining, and the like.

Purification of Methacrylic Acid or Ester Thereof:

In the step (b3), methacrylic acid or an ester thereof may be purified.

Examples of the purification method of methacrylic acid or an ester thereof include distillation, crystallization, sublimation, washing with a liquid, filtration, and combinations thereof. As the purification method of methacrylic acid or an ester thereof, distillation or crystallization is preferred, and distillation is more preferred.

The distillation can be carried out in a known manner.

As a distillation column, use can be made of common distillation columns, for example, sieve trays, dual trays, bubble cap trays, Sulzer packing, Techno pack, Mellapack, Raschig rings, Pall rings, cascade mini-rings, and combinations thereof.

In the distillation, a polymerization inhibitor may be added.

As the polymerization inhibitor, use can be made of hydroquinone, monomethyl ether of hydroquinone, phenothiazine, hindered amine radical scavenger compound, catechols (tert-butylcatechol, di-tert-butylcatechol, etc.), and the like. In addition, the presence of an oxygen-containing gas is also effective for inhibiting polymerization. Moreover, a metal containing copper can also inhibit the polymerization.

In the case where the polymerization inhibitor is not added, in order to prevent unintended polymerization, it is preferable to select a distillation column type having a small residential portion.

The temperature and pressure in the distillation operation may be conditions employed in conventional distillation of methacrylic acid or an ester thereof. For example, with regard to the temperature, in order to suppress polymerization in the column bottom, a temperature not exceeding 80° C. can be selected, and the vapor pressure is determined in response to the setting of the temperature.

The crystallization can be performed in a known manner. For example, by utilizing temperature-dependency or pressure-dependency of the solubility of methacrylic acid or an ester thereof, methacrylic acid or an ester is crystallized from a solution by cooling, pressure reduction or the like and thus selectively separated.

Methyl methacrylate is sometimes obtained as a mixture with methanol. Methyl methacrylate and methanol are known to form an azeotrope. In that case, methyl methacrylate and methanol are recovered by a method of performing distillation by using an azeotropic solvent or a method of separating them by utilizing layer separation (JP-A-H11-124347).

Since impurities can be removed by performing purification, the range of use applications of methacrylic acid or an ester thereof obtained according to the present invention is widened and also it becomes possible to produce high-quality polymer materials having more excellent heat resistance and transparency and no coloration.

(Step (c1))

The method of reacting hydrogen chloride with oxygen molecule to obtain chlorine molecule includes the method described in PETROTECH, vol. 29, No. 2, 2006, pp. 109-

113, the method described in Japanese Patent No. 3606051 and the method described in Japanese Patent No. 4192354. That is, hydrogen chloride and oxygen molecule are supplied to a fixed bed reactor filled with a catalyst in which $Ru_2O$ is supported on a rutile type $TiO_2$ carrier, and are subjected to a vapor-phase reaction to obtain chlorine molecule and water. The resulting chlorine molecule may be purified in a known manner.

<Method (β)>

The method (β) is a method containing:

(a1) a step of reacting acetone with chlorine molecule to obtain hexachloroacetone and hydrogen chloride, (a2) a step of reacting hexachloroacetone obtained in the step (a1) with an alkyl alcohol having a carbon number of from 1 to 10 to obtain a dialkyl carbonate and chloroform, (a3) if necessary, a step of reacting the dialkyl carbonate obtained in the step (a2) with phenol to obtain diphenyl carbonate and an alkyl alcohol having a carbon number of from 1 to 10 and (a4) if necessary, a step of reacting the diphenyl carbonate obtained in the step (a3) with bisphenol A to obtain an aromatic polycarbonate and phenol, (b1) a step of reacting chloroform with acetone to obtain 1,1,1-trichloro-2-methyl-2-propanol, (b4) a step of reacting the 1,1,1-trichloro-2-methyl-2-propanol obtained in the step (b1) with water or an alcohol having a carbon number of from 1 to 10 in which a part or all of hydrogen atoms bonded to carbon atoms may be replaced by halogen atom(s) and/or deuterium atom(s), in the presence of a Lewis acid catalyst at a temperature equal to or higher than the boiling point of 1,1,1-trichloro-2-methyl-2-propanol to obtain methacrylic acid or an ester thereof and hydrogen chloride, and (c2) a step of reacting the hydrogen chloride obtained in the step (a1) and the step (b4) with oxygen molecule to obtain chlorine molecule, in which, after chloroform is obtained in the step (a2), the chloroform obtained in the step (a2) is used as at least a part of chloroform in the step (b1), after the alkyl alcohol having a carbon number of from 1 to 10 is obtained in the step (a3), the alkyl alcohol having a carbon number of from 1 to 10 obtained in the step (a3) is used as at least a part of the alkyl alcohol having a carbon number of from 1 to 10 in the step (a2), after phenol is obtained in the step (a4), the phenol obtained in the step (a4) is used as at least a part of phenol in the step (a3), and after chlorine molecule is obtained in the step (c2), the chlorine molecule obtained in the step (c2) is used as at least a part of chlorine molecule in the step (a1).

The following shows a reaction scheme in the method (β).

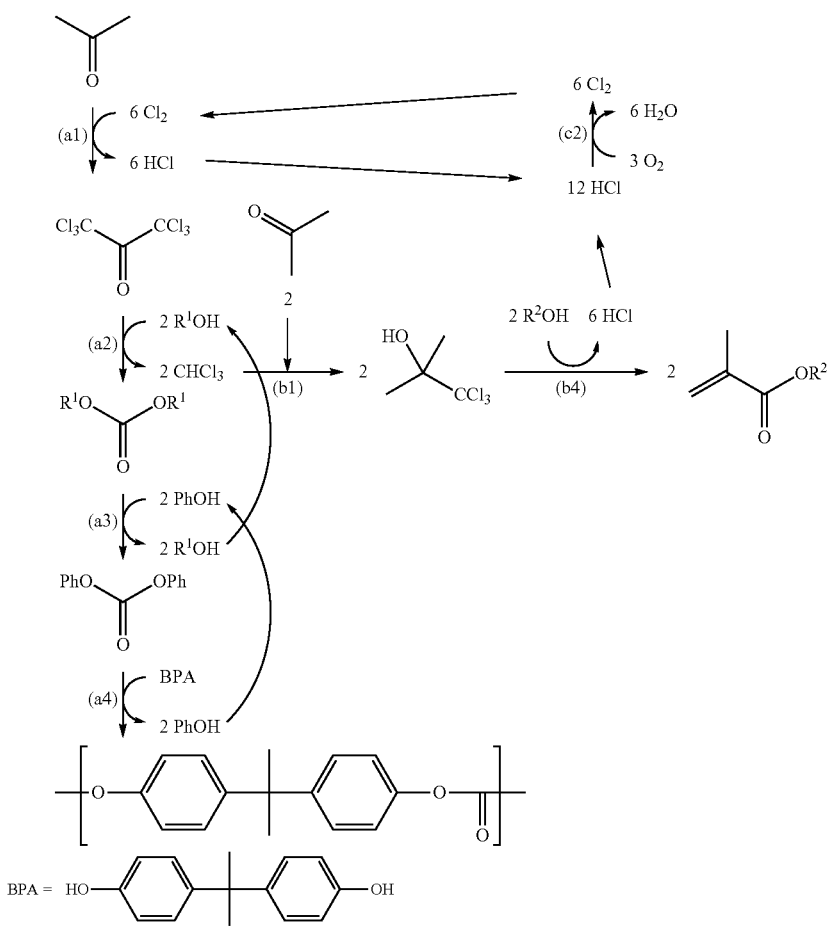

In the reaction scheme, $R^1$ is an alkyl group having a carbon number of from 1 to 10, $R^2$ is a hydrogen atom, a hydrocarbon group having a carbon number of from 1 to 10, or a group in which a part or all of hydrogen atoms bonded to the carbon atom(s) of the hydrocarbon group having a carbon number of from 1 to 10 are replaced by halogen atom(s) and/or deuterium atom(s), and Ph is a phenyl group.

As shown in the reaction scheme, in the case where the reaction ideally proceeds in 100% yield in each step in the method (β), the substance discharged into the outside of the system is water alone other than the objective products (a carbonate compound and methacrylic acid or an ester thereof). Also, in the case where the reaction ideally proceeds in 100% yield in each step in the method (β), since chlorine (hydrogen chloride and chloroform), $R^1OH$ and PhOH are all re-used in the system, it is not necessary to replenish a chlorine source, $R^1OH$ and PhOH into the system. Furthermore, in the case where the reaction ideally proceeds in 100% yield in each step in the method (β), the objective products (a carbonate compound and methacrylic acid or an ester thereof) can be obtained only by supplying acetone, bisphenol A, $R^2OH$, and oxygen molecule.

The steps (a1) to (a4), the step (b1) and the step (c2) in the method (β) are the same as the steps (a1) to (a4), the step (b1) and the step (c1) in the method (α) and thus explanations thereof are omitted.

(Step (b4))

A 1,1,1-trichloro-2-methyl-2-propanol is subjected to a reaction with water or an alcohol having a carbon number of from 1 to 10 in which a part or all of hydrogen atoms bonded to carbon atoms may be replaced by halogen atom(s) and/or deuterium atom(s), in the presence of a Lewis acid catalyst at a temperature equal to or higher than the boiling point of 1,1,1-trichloro-2-methyl-2-propanol to obtain methacrylic acid or an ester thereof and hydrogen chloride. The resulting methacrylic acid or an ester thereof may be purified in a known manner.

Alcohol:

As the alcohol, those exemplified in the step (b2) of the method (α) may be mentioned. Preferable embodiments and amount of the alcohol to be used are also the same as in the step (b2) of the method (α).

Water or the alcohol is preferably made present together with 1,1,1-trichloro-2-methyl-2-propanol from the beginning of the step (b4).

Water or the alcohol may be used as a mixture with a solvent or a diluent gas to be mentioned later.

Lewis Acid Catalyst:

Examples of the Lewis acid catalyst include one kind or a mixture of two or more kinds selected from the compounds represented by the above-mentioned formula (1) (provided that water is excluded).

As M and Y, those exemplified in the step (b2) of the method (α) may be mentioned.

As M, in view of reaction efficiency, a cation of a metal or a semi-metal selected from the group consisting of zinc, zirconium, silicon, chromium, iron, aluminum, lead, magnesium, indium, cobalt, manganese, titanium, and nickel is preferred. Of these, a cation of one or more metals or semi-metals selected from the group consisting of zinc, silicon, indium, cobalt, manganese, and nickel is particularly preferred.

As Y, an oxide ion is preferred.

Other examples of the Lewis acid catalyst include solid acids (activated clay, acid clay, zeolites, heteropoly acids, ion-exchange resins, etc.). As the activated clay, zeolites, heteropoly acids, and ion-exchange resins, those exemplified in the step (b2) of the method (a) may be mentioned.

The Lewis acid catalyst may be supported on a carrier. As the carrier, those exemplified in the step (b2) of the method (α) may be mentioned.

As the Lewis acid catalyst or the Lewis acid catalyst supported on a carrier in the step (b4), preferred are ZnO—$ZrO_2$, ZnO—$Al_2O_3$, ZnO—$TiO_2$, $In_2O_3$—$ZrO_2$, NiO—$ZrO_2$, CoO—$ZrO_2$, MnO—$ZrO_2$, active carbon, silica gel, γ-alumina, $ZrO_2$, ZnO—$SiO_2$, Zr—$PbO_x$, $Al_2O_3$—$ZrO_2$, MgO—$ZrO_2$, ZnO—$Cr_2O_3$, $TiO_2$, and Zr—$NiO_x$; more preferred are ZnO—$ZrO_2$, ZnO—$SiO_2$, $ZrO_2$, ZnO—$TiO_2$, $In_2O_3$—$ZrO_2$, NiO—$ZrO_2$, CoO—$ZrO_2$, and MnO—$ZrO_2$; and most preferred are ZnO—$ZrO_2$, ZnO—$SiO_2$, ZnO—$TiO_2$, $In_2O_3$—$ZrO_2$, and NiO—$ZrO_2$. The amount of the catalyst to be used is preferably from 0.001 mol to 1 mol, more preferably from 0.01 mol to 0.2 mol, and most preferably from 0.02 mol to 0.1 mol relative to 1 mol of 1,1,1-trichloro-2-methyl-2-propanol in the reactor in a batch-wise mode and also relative to 1 mol of 1,1,1-trichloro-2-methyl-2-propanol stayed in the reactor in a continuous mode.

In the case where the amount of the catalyst to be used is equal to or more than the lower limit, the production efficiency of methacrylic acid or an ester thereof can be improved. In the case where the amount is equal to or less than the upper limit, the volume efficiency is improved.

The mechanism of action of the Lewis acid catalyst in the step (b4) is not exactly clear but, such mechanism of action as exemplified in the following scheme is surmised. That is, in the case where methacrylic acid or an ester thereof is produced by using 1,1,1-trichloro-2-methyl-2-propanol and $R^2OH$ as raw materials and by using ZnO as a catalyst, it is surmised that the hydroxyl group in 1,1,1-trichloro-2-methyl-2-propanol and Zn interact with each other and methacrylic acid or an ester thereof is formed via a three-membered ring intermediate, dechlorination, and the like.

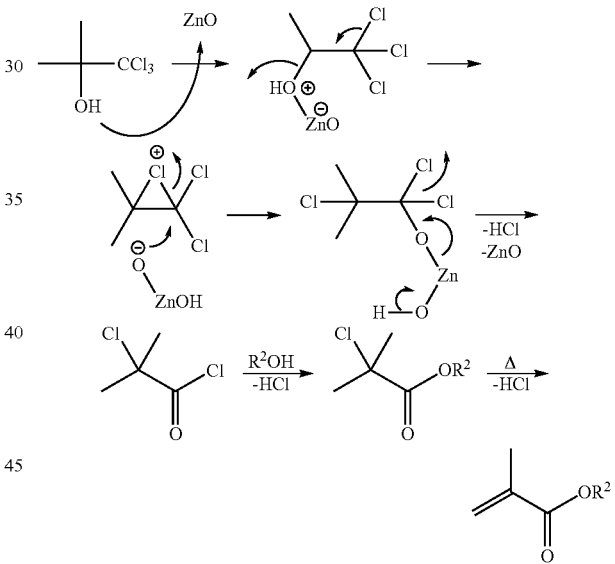

Since the Lewis acid catalyst is not consumed in the reaction as shown in the above-mentioned mechanism of action, it can be reused.

Moreover, in the case where the catalyst is deactivated, a part or whole of the catalyst may be regenerated and used. A regeneration method includes a method of heating the catalyst in a gas containing an inert gas or oxygen, a method of treating the catalyst with a hydrogen halide gas or an aqueous solution of a hydrogen halide, and a combination thereof.

Solvent or Diluent Gas:

As the solvent or diluent gas, those exemplified in the step (b2) of the method (α) may be mentioned. Preferred embodiment and amount of the solvent or diluent gas to be used is also the same as the step (b2) of the method (α).

Phase in which Reaction is Carried Out:

The reaction may be carried out in a vapor phase or may be carried out in a liquid phase. In the case where the reaction is carried out in a vapor phase, methacrylic acid or an ester thereof can be more efficiently obtained.

It depends on the boiling point of the raw material whether the reaction is carried out either in a vapor phase or in a liquid phase, but the phase can be changed as appropriate by setting the reaction temperature or reaction pressure.

Reaction Mode:

The reaction mode may be a batch-wise mode or a continuous mode.

The space velocity in the case where the reaction is carried out in a continuous mode is the same as in the step (b2) of the method (α).

Reaction Temperature:

The reaction temperature is appropriately set according to the kind of the raw material compound or the catalyst. Specifically, the reaction temperature is preferably equal to or higher than the boiling point of 1,1,1-trichloro-2-methyl-2-propanol and 350° C. or lower, more preferably from 170° C. to 350° C., and most preferably from 200° C. to 300° C. In the case where the reaction temperature is equal to or higher than the lower limit, methacrylic acid or an ester thereof can be efficiently obtained. In the case where the reaction temperature is equal to or lower than the upper limit, decomposition of the raw material and the products and an increase of side reactions are less likely to occur.

The boiling point of 1,1,1-trichloro-2-methyl-2-propanol is 169° C. (167° C. in some literature) and the boiling point of 1,1,1-trichloro-2-methyl-2-propanol 0.5 hydrate is from 173° C. to 175° C.

Reaction Pressure:

The reaction pressure is the same as in the step (b2) of the method (α).

Reaction Time:

The reaction time is the same as in the step (b2) of the method (α). In the case where the reaction is carried out in a continuous mode as a vapor phase reaction, the reaction time is preferably from 0.5 second to 30 seconds.

Reaction Apparatus:

The reaction apparatus is the same as in the step (b2) of the method (α).

Purification of Methacrylic Acid or Ester Thereof:

The method of purifying methacrylic acid or an ester thereof is the same as in the step (b3) of the method ((u).

(Action and Effect)

In the method for producing a carbonate compound and methacrylic acid or an ester thereof according to the present invention as described above, since the carbonate compound is obtained by using acetone, chlorine molecule, an alcohol, phenol, and bisphenol A as raw materials, the carbonate compound can be produced without using highly toxic gases such as phosgene and carbon monoxide.

Also, since methacrylic acid or an ester thereof is obtained by using acetone, chloroform, and water or an alcohol as raw materials, methacrylic acid or an ester thereof can be produced without using highly toxic gases such as hydrogen cyanide and carbon monoxide.

Moreover, since the raw materials are all easily available, there is no limitation on raw material availability.

Furthermore, since by-products (hydrogen chloride, chloroform, an alcohol, phenol) can be converted and purified as needed and subsequently can be reused as raw materials, the by-products can be effectively utilized and the amount of production is not limited by the demand of the by-products.

EXAMPLES

The following will specifically describe the present invention with reference to Experimental Examples and Comparative Examples but the present invention should not be construed as being limited to these examples.

Examples 1 to 34 are Experimental Examples and Comparative Examples 1 and 2 are Comparative Examples.

In the following, gas chromatography is referred to as GC.

The yield means an isolated yield unless otherwise specified.

The yield determined from a peak area ratio of an NMR spectrum is referred to as NMR yield.

The purity determined from a peak area ratio of GC is referred to as GC purity.

The pressure is gauge pressure unless otherwise specified.

The reaction where a compound sensitive to oxygen or moisture was handled was carried out under a nitrogen stream.

Example 1

Step (a1)

Into a nickel-made reactor having an inner volume of 3 L and equipped with a condenser was charged 36.1 g of a dried product of powdery activated carbon (manufactured by Japan Enviro Chemicals Co., Ltd.; type: powdery Sirasagi activated carbon; average particle diameter: 45 m; specific surface area: 876 m$^2$/g), and chlorine molecule was supplied thereinto at 0.3 L/min for one hour. To the reactor was added 1,750 g of hexachloroacetone (manufactured by Aldrich) as a solvent, stirring was started, and the inner temperature was raised to 150° C. Chlorine molecule was further supplied thereinto at 10.6 mol/hr. After 5 minutes from the start of the supply of chlorine molecule, acetone was supplied at 1.3 mol/hr and heat removal was performed so that the temperature became 150° C. to 155° C. After 300 minutes from the start of the supply of acetone, the supply of acetone was stopped. The flow rate of chlorine molecule was changed to 5.3 mol/hr and the reaction was further continued for 1 hour. Acetone was supplied in an amount of 394 g (6.79 mol) in total and chlorine molecule were supplied in an amount of 4,496 g (63.41 mol), so that the molar ratio of the charged chlorine molecule and acetone (chlorine molecule/acetone) was 9.34.

The gas discharged from the reactor was allowed to pass through an absorption column cooled to 0° C., which contained 634 g of hexachloroacetone as an absorption liquid, a cooling trap at −20° C., and an about 20% by mass aqueous sodium hydroxide solution, so that organic substances such as hexachloroacetone, chloroacetones having 1 to 5 chlorine atoms, and acetone were recovered in the absorption column and the cooling trap and chlorine molecule and hydrogen chloride were absorbed in the aqueous sodium hydroxide solution.

As a result of analysis of the reaction mixture in the reactor by GC using an internal standard, the yield of hexachloroacetone formed by the reaction was 94%, and the total yield of chloroacetones having 1 to 6 chlorine atoms was 99%. The resulting reaction mixture was filtered by using a polytetrafluoroethylene filter having a pore size of 0.2 μm to obtain a crude product. When the crude product was distilled, 0.4% by mass of high-boiling compounds was confirmed relative to the crude product.

Example 2

Step (a2)

Into a three-necked glass-made reactor having an inner volume of 10 L and equipped with a dropping funnel and a distillation line whose cooling part was cooled to 10° C. were charged 50 g of K$_2$CO$_3$ (reagent of Tokyo Chemical Industry Co., Ltd., P1748) and 3,408 g (46.0 mol) of 1-butanol (reagent of Tokyo Chemical Industry Co., Ltd., B0704). After the whole was warmed to 30° C. on an oil bath, the whole amount of 4,154 g (15.7 mol) of hexachloroacetone (reagent of Tokyo Chemical Industry Co., Ltd., H0335) was added dropwise from the dropping funnel with stirring while adjusting the dropping rate so that the temperature in the reactor did not exceed 50° C. After completion of the dropwise addition, the oil bath temperature was gradually elevated to 100° C. over a period of two hours while performing sufficient stirring. Chloroform formed by the reaction in the course of temperature elevation was recovered as a liquid from a distillation line installed in the reactor. From the time when the oil bath temperature reached 100° C., the pressure in the system was gradually reduced by a vacuum pump through a pressure regulating valve installed in the distillation line, and pressure reduction was continued until the pressure finally reached 20 mmHg. An excess 1-butanol and dibutyl carbonate formed by the reaction in the reactor were withdrawn from the distillation line, and the distillation was continued until no liquid finally remained in the reactor, thereby recovering the whole amount (7,486 g, recovery rate 99%) of the reaction mixture. The reaction mixture was charged into a distillation column having a theoretical plate number of 20 stages, and distillation was performed under reduced pressure while adjusting the pressure so that the inner temperature of the distillation still did not become 120° C. or higher. As a result of the distillation, 2,614 g (yield 95.5%) of a reaction mixture containing dibutyl carbonate having a GC purity of 99.8% was recovered.

Example 3

Step (a3)

According to the method described in JP-A-2006-335739, vanadium phenoxide was synthesized by using vanadium oxide as a starting material.

By using the vanadium phenoxide as a catalyst, an ester exchange reaction and a disproportionation reaction were carried out according to known methods for the dibutyl carbonate synthesized in Example 2 to synthesize diphenyl carbonate. Diphenyl carbonate having a GC purity of 99.5% was recovered by distillation.

Example 4

Step (a4)

Into a round-bottom four-necked flask having an inner volume of 300 mL, equipped with a distillation part consisting of an air-cooler (15 mm diameter×200 mm) and a receiver and further equipped with a stirrer (manufactured by Nakamura Scientific Instruments Industry Co., Ltd., MS-8) and a stirring blade were charged 30.00 g (0.140 mol) of diphenyl carbonate, 31.19 g (0.137 mol) of bisphenol A and NaHCO$_3$ (1.0 µmol per mole of bisphenol A). After drying for one hour while reducing the pressure in the system by a rotary pump, the pressure was raised to normal pressure by nitrogen gas and the whole was immersed in an oil bath at 180° C.

After the contents were melted, polymerization was initiated at an oil bath temperature of 205° C. under a pressure of 200 mmHg. While confirming the progress of the polymerization by the amount of phenol generated in the system, the oil bath temperature and the pressure in the system were gradually changed. Finally reached conditions were as follows: oil bath temperature was 280° C., and pressure in the system was less than 1 mm Hg. The polymerization was finished at the time when stirring became impossible due to an increase in viscosity.

Example 5

Step (b1)

Into a three-necked flask having an inner volume of 100 mL were charged 36.7 g (0.63 mol) of acetone and 15.0 g (0.13 mol) of chloroform, followed by cooling to −10° C. Thereto was added 3.0 g (0.008 mol) of a 50% by mass aqueous sodium hydroxide solution separately prepared, followed by stirring for 20 minutes, and then, the temperature was slowly raised to room temperature. A part of the resulting crude reaction liquid was sampled and analyzed by GC with adding dichloromethane as an internal standard. As a result of the analysis, the conversion rate of chloroform was 49%, and selectivity of 1,1,1-trichloro-2-methyl-2-propanol (hereinafter referred to as TCMP) on the basis of chloroform was 92%.

Example 6

Step (b2)

Into a three-necked flask having an inner volume of 50 mL and equipped with a Dimroth condenser were charged 15.14 g (0.080 mol) of TCMP 0.5 hydrate, 2.00 g (0.016 mol, 0.2 mol relative to 1 mol of TCMP) of zinc chloride, followed by heating until the inner temperature reached 125° C. while stirring, and the whole was held for 30 minutes in that state. After the reactor was cooled, a part of the resulting crude reaction liquid was sampled and analyzed by GC with adding dichloromethane as an internal standard.

As a result of the analysis, it was found, as shown below, that the conversion rate of TCMP was 85.4% and the yield of 2-chloro-2-methylpropanoic acid was 54.4%. As other products, methacrylic acid was obtained in 2.3% yield, (1,1,1-trichloro-2-methyl-2-propyl) methacrylate was obtained in 22.7% yield, and (1,1,1-trichloro-2-methyl-2-propyl) 2-chloro-2-methylpropanoate was obtained in 7.8% yield.

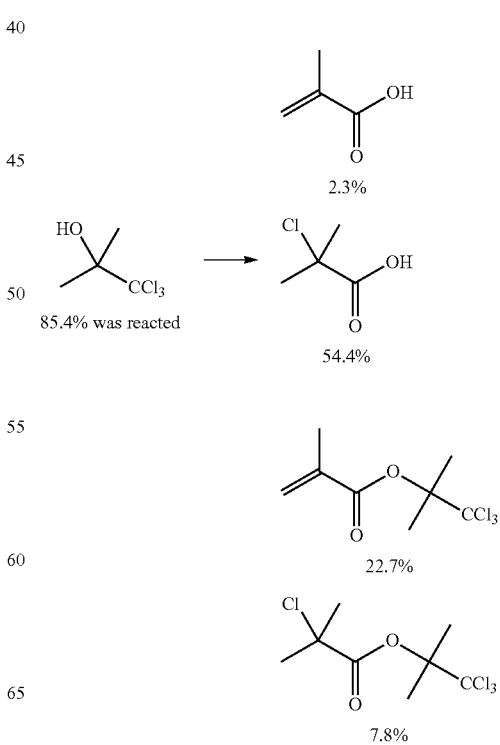

Example 7

Step (b2)

A nitrobenzene solution containing 12.1% by mass of TCMP was obtained by mixing 30.55 g of TCMP 0.5 hydrate and 213.31 g of nitrobenzene and drying over molecular sieves 4A. A reaction was carried out in the same manner as in Example 6 except that 30.80 g of the solution (containing 3.7 g (0.021 mol) of TCMP) and 0.14 g (0.001 mol, 0.05 mol relative to 1 mole of TCMP) of zinc chloride were used, the reaction temperature was controlled to 105° C., the reaction time was controlled to 14 hours, and the reaction was performed while allowing a nitrogen gas to flow through the reactor at 100 mL/min.

To 2.83 g of the resulting crude reaction liquid was added 0.11 g of methanol, followed by heating at 60° C. for 4 hours, and then analysis by GC was performed. As a result of the analysis, it was found that the conversion rate of TCMP was 86.0% and the yield of methyl 2-chloro-2-methylpropanoate was 10.2%. As other products, methyl methacrylate (hereinafter referred to as MMA) was obtained in 0.2% yield, methacrylic acid (hereinafter referred to as MAA) was obtained in 8.7% yield, (1,1,1-trichloro-2-methyl-2-propyl) methacrylate was obtained in 13.1% yield, and (1,1,1-trichloro-2-methyl-2-propyl) 2-chloro-2-methylpropanoate was obtained in 22.8% yield.

Example 8

Step (b2)

As in Example 7, a nitrobenzene solution containing 12.3% by mass of TCMP was obtained. In a three-necked flask having an inner volume of 50 mL equipped with a Dimroth condenser, 40.68 g (containing 5.0 g (0.029 mol) of TCMP) of the nitrobenzene solution of TCMP, 0.18 g (0.001 mol, 0.03 mol relative to 1 mol of TCMP) of zinc chloride and 1.28 g of methanol were mixed and they were subjected to a reaction at 115° C. for 1 hour and at 130° C. for 1 hour. After 3.00 g of methanol was further added and a reaction was carried out at 85° C. for 10 minutes, analysis was performed by GC.

By the analysis of the crude reaction liquid by GC, it was found that the conversion rate of TCMP was 70.0% and the yield of methyl 2-chloro-2-methylpropanoate was 23.9%. As other products, MMA was obtained in 0.7% yield, MAA was obtained in 0.2% yield, (1,1,1-trichloro-2-methyl-2-propyl) methacrylate was obtained in 7.8% yield, and (1,1,1-trichloro-2-methyl-2-propyl) 2-chloro-2-methylpropanoate was obtained in 12.9% yield.

Example 9

Step (b2)

As in Example 7, a nitrobenzene solution containing 12.1% by mass of TCMP was obtained. A reaction was carried out in the same manner as in Example 6 except that 999.92 g (containing 120 g (0.68 mol) of TCMP) of the solution and 99.51 g (0.68 mol, 1 mol relative to 1 mol of TCMP) of zinc chloride were used and the reaction time was changed to 6 hours. At this time, when titration was performed after the gas discharged from the reactor was absorbed into an aqueous sodium hydroxide solution, it was found that 0.638 mol of hydrogen chloride was generated. After the resulting crude reaction liquid was filtered by suction filtration, 37.37 g of methanol was mixed therein and the whole was heated at 60° C. for 5 hours.

By the analysis of the crude reaction liquid by GC, it was found that the conversion rate of TCMP was 67.7% and the yield of methyl 2-chloro-2-methylpropanoate was 36.5%. As other products, (1,1,1-trichloro-2-methyl-2-propyl) methacrylate was obtained in 10.5% yield and (1,1,1-trichloro-2-methyl-2-propyl) 2-chloro-2-methylpropanoate was obtained in 13.5% yield. The obtained crude reaction liquid was distilled under reduced pressure to obtain methyl 2-chloro-2-methylpropanoate having a purity of 85%.

Example 10

Step (b2)

Into a three-necked flask having an inner volume of 3 L were charged 502.8 g (2.696 mol) of TCMP 0.5 hydrate and 1,507 g (15.23 mol) of 1,2-dichloroethane, then a distillation column was fitted thereto, an azeotropic mixture of 1,2-dichloroethane and water was distilled off, and further concentration was performed. The distillation column was replaced by a reflux condenser and 551.6 g (5.624 mol) of sulfuric acid was added thereto dropwise over a period of 40 minutes while maintaining the inner temperature at 35° C. or lower. After the completion of the dropwise addition, vigorous generation of hydrochloric acid gas was observed. Stirring was continued as it was over night. Thereto was further added 259.7 g (8.111 mol) of methanol over a period of 60 minutes, followed by heating to 60° C. and stirring for 6 hours.

The reflux condenser was replaced by a distillation column, the pressure of the system was reduced to 5.3 kPa, and a fraction having a boiling point up to 52° C. was distilled out to obtain 401.0 g of a crude liquid. The crude liquid was distilled by using a distillation column to obtain 306.8 g (2.246 mol, boiling point: 133° C. to 134° C., yield: 83%) of methyl 2-chloro-2-methylpropanoate having a GC purity of 99% or more.

$^1$H-NMR (300.4 MHz, CDCl$_3$, TMS) δ; 1.79 (s, 6H), 3.80 (s, 3H).

Example 11

Step (b2)

Into a three-necked flask having an inner volume of 200 mL were charged 12.7 g (68.3 mmol) of TCMP 0.5 hydrate and 48.6 g (491 mmol) of 1,2-dichloroethane, then a distillation column was fitted thereto, an azeotropic mixture of 1,2-dichloroethane and water was distilled off, and further concentration was performed. The distillation column was replaced by a reflux condenser and 2.00 g (20.4 mmol) of sulfuric acid was added thereto. Stirring was continued as it was at 90° C. for 14 hours. After cooling to room temperature, 6.60 g (200 mmol) of methanol was added thereto and the whole was heated to 60° C. and stirred for 5.5 hours.

The contents were added to 80 g of water and extraction was performed once with 40 mL of dichloromethane and three times with 20 mL thereof. The organic layer was washed twice with 20 mL of brine, dried over magnesium sulfate and then concentrated to obtain 13.7 g of a crude liquid. It was found by NMR analysis that the crude liquid contained 6.69 g (49.0 mmol) of methyl 2-chloro-2-methylpropanoate. The NMR yield was 72%.

Example 12

Step (b2)

Into a three-necked flask having an inner volume of 100 mL was charged 12.7 g (68.0 mmol) of TCMP 0.5 hydrate, then a reflux condenser was fitted thereto, and 13.5 g (136 mmol) of sulfuric acid was added thereto. The whole was stirred as it was at room temperature for 7 hours, thereto was further added 13.4 g (135 mmol) of sulfuric acid, followed by stirring at room temperature for 16 hours. Further, 10.9 g (340 mmol) of methanol was added and the whole was heated to 60° C. and stirred for 6 hours.

The contents were added to 100 g of ice water and extraction was performed once with 40 mL of dichloromethane and three times with 20 mL thereof. The organic layer was washed twice with 20 mL of brine, dried over magnesium sulfate and concentrated to obtain 12.2 g of a crude liquid. It was found by NMR analysis that the crude liquid contained 8.76 g (64.2 mmol) of methyl 2-chloro-2-methylpropanoate. The NMR yield was 94%.

Example 13

Step (b2)

A 1,2-dichloroethane solution containing 28% by mass of TCMP was obtained by mixing TCMP 0.5 hydrate and 1,2-dichloroethane and drying over molecular sieves 4A. In a three-necked flask fitted with a Dimroth condenser at the outlet, 10 g (containing 2.89 g (0.016 mol) of TCMP) of the solution, 20 g of 1,2-dichloroethane and 4.26 g of activated clay (F-24X, manufactured by N.E. CHEMCAT Corporation) were mixed under a nitrogen stream and the whole was heat at 50° C. for 2 hours and then heated at 95° C. under reflux for 8 hours. Thereafter, thereto was further added dropwise 1.56 g (0.049 mol) of methanol through a dropping funnel, followed by heating at 85° C. under reflux for 4 hours. After a crude reaction liquid was obtained, it was analyzed by GC with adding dichloromethane as an internal standard.

As a result of the analysis, the conversion rate of TCMP was 99.0%, the yield of methyl 2-chloro-2-methylpropanoate was 55.6% on the basis of TCMP, the yield of 1,1,3-trichloro-2-methylpropene was 17.5%, and the yield of (1,1,1-trichloro-2-methyl) 2-chloro-2-methylpropanoate was 6.4%.

Example 14

Step (b2)

A 1,2-dichloroethane solution containing 28% by mass of TCMP was obtained by mixing TCMP 0.5 hydrate and 1,2-dichloroethane and drying over molecular sieves 4A. In a three-necked flask connected with a Dimroth condenser at the outlet and with an aqueous sodium hydroxide solution beyond the Dimroth condenser, 50.1 g (containing 14.0 g (0.079 mol) of TCMP) of the solution and 16.0 g (0.164 mol) of sulfuric acid were mixed under a nitrogen stream to carry out a reaction for 1 hour. The liquid after completion of the reaction was separated into two layers and 43.6 g of an upper layer and 16.3 g of a lower layer were recovered. By NMR analysis, it was confirmed that the upper layer contained 50.1 g (0.365 mol) of 1,2-dichloroethane, 0.053 mol of 2-chloro-2-methylpropanoyl chloride, and 0.005 mol of 2-chloro-2-methylpropanoic sulfuric anhydride; and the lower layer contained 0.010 mol of 2-chloro-2-methylpropanoic sulfuric anhydride. Moreover, by titration of the aqueous sodium hydroxide solution, generation of acidic gas corresponding to 0.078 mol was confirmed. This was 2.8 g in terms of hydrogen chloride, which corresponded to 99% yield on the basis of TCMP used.

Example 15

Step (b2)

By using the same apparatus as in Example 14, 2.8 g (0.087 mol) of methanol was added to the upper layer liquid obtained in Example 14, followed by carrying out a reaction at room temperature for 4 hours. By NMR analysis of the resulting liquid, the formation of 0.060 mol of methyl 2-chloro-2-methylpropanoate was confirmed. This corresponds to 76% yield on the basis of TCMP used in the reaction in Example 14. Moreover, by titration of the aqueous sodium hydroxide solution, generation of acidic gas corresponding to 0.049 mol was confirmed. This was 1.8 g in terms of hydrogen chloride, which corresponded to 62% yield on the basis of TCMP used in Example 14.

Example 16

Step (b2)

Into a three-necked flask equipped with a cooling trap at the outlet of the reactor was charged 17.3 g of sulfuric acid and then the pressure was reduced to 20 mmHg by using a diaphragm pump. An aqueous sodium hydroxide solution was connected to the outlet of the diaphragm pump.

The inner temperature of the reactor was maintained at 50° C. and, while adding a 52.2% by mass normal octane solution of TCMP at a rate of 0.94 g per minute, a fraction was recovered by the cooling trap. The solution was continuously added for 520 minutes and 486.8 g of the raw material solution was added in total, thereby obtaining 365.6 g as the fraction. By NMR analysis of the obtained solution, the formation of 837.5 mol of 2-chloro-2-methylpropanoyl chloride was confirmed. This corresponds to 58.8% yield on the basis of TCMP used. Moreover, by titration of the aqueous sodium hydroxide solution, generation of acidic gas corresponding to 1.18 mol was confirmed. This was 43.0 g in terms of hydrogen chloride, which corresponded to 82% yield on the basis of TCMP used.

Summary of Examples 6 to 16

As shown in Examples 6 to 16, objective compounds could be obtained in a catalyst amount of 0.03 mol to 1 mol relative to 1 mole of TCMP. In addition, the chlorine in TCMP could be obtained in the form of hydrogen chloride. In the above experimental examples, zinc chloride, sulfuric acid, or activated clay was used as a catalyst, but it is needless to say that similar reactions can be conducted with the other Lewis acid catalysts.

Example 17

Step (b3)

An Inconel-made tube having an inner diameter of 4.35 mm was heated to 520° C. in an electric furnace having a full-length of 30 cm. Through this, nitrogen (516 mL/hr) and methyl 2-chloro-2-methylpropanoate (2.65 g/hr) were allowed to flow simultaneously for 4 hours. Products were collected by a dry-ice trap. Thus, 10.6 g (77.7 mmol) of methyl 2-chloro-2-methylpropanoate was charged and 9.05 g of a liquid was trapped in the dry-ice trap. By NMR analysis, it was found that the liquid contained 5.15 g (51.4 mmol) of MMA and 2.91 g (21.3 mmol) of methyl 2-chloro-2-methylpropanoate. The conversion rate of methyl 2-chloro-2-methylpropanoate was 73% and the selectivity of MMA was 91%.

Example 18

Step (b4)

A 5% by mass zirconium-supported zinc oxide (5% $ZnO$—$ZrO_2$) catalyst was obtained by an impregnation method.

The 5% $ZnO$—$ZrO_2$ catalyst was filled in an amount of 8.2 g into a glass tube having a length of 30 cm and an inner diameter of 14 mm and the temperature was maintained at 200° C. While nitrogen gas was fed at a flow rate of 0.05 L/min into the glass tube, a 50% by mass TCMP 0.5 hydrate dissolved in methanol was fed at a flow rate of 10.0 g/hr to conduct a reaction in a vapor phase. In the present Example, 26.5 g of a 50% by mass TCMP 0.5 hydrate methanol solution, that is, 12.6 g (0.071 mol) of TCMP was fed. A gas obtained by the reaction was cooled with dry ice to obtain a crude reaction liquid. In the present Example, 22.6 g of the crude reaction liquid was obtained.

Analysis by GC for the crude reaction liquid was performed by using dichloromethane as an internal standard. For example, for MMA, the yield was determined as follows.

The concentration Z (mol/g) of MMA in the crude reaction liquid was measured by GC. A total amount T (mol) of MMA obtained by the reaction was calculated according to an equation of "$T = Z \times W$". W is the obtained crude reaction liquid (g). Moreover, the yield Y (%) of MMA was calculated according to an equation of "$Y = (T/X) \times 100$". X is an amount (mol) of TCMP used.

Examples 19 to 32

Step (b4)

Crude reaction liquids were obtained by performing reactions in the same manner as in Example 18 except that the kind of the catalyst, the amount of the catalyst filled, reaction temperature, flow rates of the TCMP solution and nitrogen gas, the amount of the TCMP solution, and the amount X (mol) of TCMP used were changed as shown in Table 1. As in Example 18, analysis by GC was performed for the crude reaction liquids.

Table 2 shows the results of Examples 18 to 32, the amounts (g) of the resulting crude reaction liquids, yields (mol) of MMA, conversion rates of TCMP, and yields (%) of methyl 2-chloro-2-methylpropanoate, MMA and MAA on the basis of TCMP.

Comparative Example 1

In a 50 ml eggplant-shaped flask fitted with a Dimroth condenser was charged 1.4 g of the 5% $ZnO$—$ZrO_2$ catalyst obtained by an impregnation method in the same manner as in Example 18.

Thereto were added 3.0 g (16.9 mmol) of TCMP and 0.5 g (16.9 mmol) of methanol.

The whole was stirred at 140° C. for 1 hour by a stirrer to carry out a reaction in a liquid phase. After stirring, the whole was cooled to room temperature and the catalyst was removed.

TABLE 1

| | | Catalyst | | Reaction | Flow rate of | Flow rate | Amount of | Amount X of |
|---|---|---|---|---|---|---|---|---|
| | | Kind | Filling amount (g) | temperature (° C.) | TCMP solution (g/hr) | of $N_2$ (L/min) | TCMP solution (g) | TCMP in solution (mol) |
| Example | 18 | 5% $ZnO$—$ZrO_2$ | 8.2 | 200 | 10.0 | 0.05 | 26.5 | 0.071 |
| | 19 | 5% $ZnO$—$ZrO_2$ | 8.9 | 250 | 10.0 | 0.05 | 28.2 | 0.0756 |
| | 20 | 10% $ZnO$—$ZrO_2$ | 9.5 | 250 | 2.8 | 0.10 | 11.3 | 0.0303 |
| | 21 | Silica gel | 3.8 | 250 | 2.8 | 0.05 | 9.0 | 0.0241 |
| | 22 | γ-alumina | 7.3 | 250 | 10.5 | 0.05 | 32.4 | 0.0869 |
| | 23 | $ZrO_2$ | 8.3 | 250 | 2.8 | 0.10 | 11.3 | 0.0303 |
| | 24 | $ZnO$—$SiO_2$ | 9.5 | 200 | 10.0 | 0.05 | 26.4 | 0.0708 |
| | 25 | $Zr \cdot PbO_x$ | 12.4 | 200 | 10.0 | 0.05 | 25.9 | 0.0694 |
| | 26 | $MgO$—$ZrO_2$ | 10.0 | 250 | 10.5 | 0.05 | 32.4 | 0.0869 |
| | 27 | $ZnO$—$Cr_2O_3$ | 10.0 | 250 | 2.8 | 0.10 | 11.1 | 0.0298 |
| | 28 | $Zr$—$NiO_x$ | 12.2 | 250 | 2.7 | 0.10 | 11.0 | 0.0295 |
| | 29 | 1.6% $In_2O_3$—$ZrO_2$ | 11.6 | 200 | 10.0 | 0.05 | 24.9 | 0.0702 |
| | 30 | 10% $NiO$—$ZrO_2$ | 6.4 | 200 | 10.0 | 0.05 | 25.3 | 0.0713 |
| | 31 | 10% $CoO$—$ZrO_2$ | 6.5 | 200 | 10.0 | 0.05 | 24.7 | 0.0696 |
| | 32 | 10% $MnO$—$ZrO_2$ | 6.4 | 200 | 10.0 | 0.05 | 24.4 | 0.0687 |
| Comparative Example 1 | | 5% $ZnO$—$ZrO_2$ | 1.4 | 140 | — | — | 3.5 | 0.0169 |

TABLE 2

| | | Crude reaction liquid W (g) | MMA concentration Z in crude reaction liquid (mol/g) | MMA yield T (mol) | MMA yield Y (%) |
|---|---|---|---|---|---|
| Example | 18 | 22.6 | 0.00227 | 0.0514 | 72.3 |
| | 19 | 20.0 | 0.00266 | 0.0531 | 70.2 |
| | 20 | 6.2 | 0.00206 | 0.0128 | 42.3 |
| | 21 | 6.1 | 0.00016 | 0.00097 | 4.0 |
| | 22 | 30.0 | 0.00014 | 0.0042 | 4.8 |
| | 23 | 8.9 | 0.00047 | 0.0042 | 13.9 |
| | 24 | 19.4 | 0.00235 | 0.0456 | 64.4 |
| | 25 | 25.1 | 0.00007 | 0.0018 | 2.6 |
| | 26 | 31.7 | 0.00007 | 0.0023 | 2.6 |
| | 27 | 9.0 | 0.00041 | 0.0037 | 12.4 |
| | 28 | 9.2 | 0.00026 | 0.0024 | 8.1 |
| | 29 | 21.7 | 0.00221 | 0.048 | 74.5 |
| | 30 | 21.7 | 0.00182 | 0.0396 | 60.2 |
| | 31 | 22.6 | 0.00151 | 0.0341 | 48.0 |
| | 32 | 22.6 | 0.00099 | 0.0224 | 35.8 |
| Comparative Example 1 | | 3.47 | 0.00004 | 0.00012 | 0.7 |

From the above results, it was shown that MMA in sufficient yields was obtained in Examples 18 to 32 in which the reactions were carried out at a high temperature by using the Lewis acid catalyst. That is, it was proved that MMA was obtained in one stage from raw materials TCMP and methanol. Of these, in Examples 18 to 20, 24, and 29 to 32 in which ZnO—ZrO$_2$, ZnO—SiO$_2$, In$_2$O$_3$—ZrO$_2$, NiO—ZrO$_2$, CoO—ZrO$_2$, or MnO—ZrO$_2$ was used as a catalyst, the yields of MMA were relatively high. In particular, in Examples 18 to 20, 24, 29, and 30 in which ZnO—ZrO$_2$, ZnO—SiO$_2$, In$_2$O$_3$—ZrO$_2$, or NiO—ZrO$_2$ was used, the yields were remarkably high. On the other hand, in Comparative Example 1 in which the reaction was carried out at 140° C., a sufficient amount of MMA was not obtained.

As a factor for the remarkably high yield of MMA in Examples 18 to 32, there may be mentioned the fact that the reaction was carried out in a vapor phase. In the case of carrying out the reaction in a liquid phase, it is highly possible that methanol acts as a Lewis base and combines with the Lewis acid catalyst to deactivate the catalytic function thereof. On the other hand, in the case of carrying out the reaction in a vapor phase, since methanol becomes a gas, the concentration thereof in the reaction field is low and methanol is difficult to deactivate the Lewis acid catalyst. It is considered that the catalytic reaction easily proceeds for this reason and, as a result, MMA is formed in high yields. Accordingly, when the present reaction is carried out in a vapor phase, a methacrylate ester is more efficiently obtained. Thus, since the boiling point of TCMP is 169° C., it has been concluded that the effect of the present invention is more enhanced when the reaction temperature is set at 170° C. or higher.

Example 33

Step (b4)

In the present Example, water was used as a raw material instead of methanol and the reaction temperature was changed to 200° C.

Into a Hastelloy C-276-made metal tube (manufactured by Morimoto Seikan Co.) having a length of 20 cm and an inner diameter of 21.3 mm (hereinafter referred to as reaction tube) was filled 43.12 g of a 5% ZnO—TiO$_2$ catalyst prepared by an impregnation method as in Example 18, and the temperature was maintained at 200° C.

In the present Example, in order to perform the reaction more efficiently, raw materials were gasified beforehand. Specifically, a Hastelloy C-276-made metal tube (pre-heating tube) heated to 200° C. was prepared separately from the reaction tube, and 85% by weight TCMP dissolved in chloroform and water were fed into the pre-heating tube at flow rates of 57.3 g/hr and 4.9 g/hr, respectively, and were gasified. The formed gas was mixed with nitrogen of a flow rate of 29.5 mL/min and fed into the reaction tube to be subjected to a reaction for 3 hours. The feed amount of the 85% by mass chloroform solution of TCMP was 164.5 g and the feed amount of water was 13.3 g.

The gas obtained by the reaction was cooled with dry ice to obtain 114.7 g of a crude reaction liquid. In addition, a hydrogen chloride gas produced as a by-product was recovered by absorbing it into potassium hydroxide.

By using dichloromethane as an internal standard, the concentration of MAA in the crude reaction liquid was measured by GC.

As in Examples 18 to 32, the total amount and yield of MAA and the amount of hydrogen chloride were calculated.

As a result, the yield of MAA was 70.1%, 55.01 g of hydrogen chloride was recovered, and the recovery rate of hydrogen chloride relative to a theoretical value was 74.6%.

Comparative Example 2

In the present Comparative Example, a reaction was carried out in the same manner as in Comparative Example 1 except that 0.3 g (16.9 mmol) of water was used as a raw material of the reaction instead of methanol to obtain 3.47 g of a crude reaction liquid.

In Examples 18 to 20 and 33 and Comparative Example 2, the concentration of MAA in the crude reaction liquid was measured by GC using dichloromethane as an internal standard and the yield of MAA was calculated.

Table 3 shows the yields of MAA in Examples 18 to 20 and 33 and Comparative Example 2.

TABLE 3

|  |  | MAA yield (%) |
| --- | --- | --- |
| Example | 18 | 6.7 |
|  | 19 | 7.5 |
|  | 20 | 6.7 |
|  | 33 | 70.1 |
| Comparative Example 2 |  | 0.31 |

From the above results, it was proved that MAA was obtained in one stage from raw material TCMP and water. Particularly, it was shown that MAA was efficiently obtained when the reaction was carried out in a vapor phase.

Example 34

Step (b4)

In the present Example, mass production of MMA by the step (b4) was investigated.

A 5% ZnO—ZrO$_2$ catalyst obtained by an impregnation method as in Example 18 was filled in an amount of 77.5 g into the same reaction tube as that used in Example 33 and the temperature was maintained at 200° C.

In the present Example, in order to perform the reaction more efficiently, before feeding to the reaction tube, raw materials were gasified beforehand. Specifically, a Hastelloy C-276-made metal tube (pre-heating tube) heated to 170° C. was prepared separately from the reaction tube, and 85% by mass TCMP dissolved in acetone and methanol were fed into the pre-heating tube at flow rates of 13.17 g/hr and 16.9 g/hr, respectively, and were gasified. The formed gas was mixed with nitrogen at a flow rate of 27.4 mL/min and fed into the reaction tube. A reaction was carried out for 11.5 hours. The feed amount of the 85% by mass acetone solution of TCMP was 155.5 g and the feed amount of methanol was 187.6 g.

The gas obtained by the reaction was cooled by an ice bath to obtain 216.0 g of a crude reaction liquid. In addition, 113.2 g of chloromethane was collected from the vapor phase part.

By using tetraethylene glycol dimethyl ether as an internal standard, the concentration of MMA in the crude reaction liquid was measured by GC.

As a result of calculation of the total amount and yield of MMA as in Examples 18 to 33, the yield of MMA was 93.9%.

INDUSTRIAL APPLICABILITY

The aromatic polycarbonates obtained by the production method of the present invention have been widely used in many fields as engineering plastics excellent in heat resistance, impact resistance, transparency, and the like. Methacrylate esters are excellent in transparency and weather resistance and have been widely used as monomers of methacrylic resins which have been used as illumination devices, automobile parts, building-related materials, and flat display materials.

Although the present invention has been described in detail and by reference to the specific embodiments, it is apparent to one skilled in the art that various modifications or changes can be made without departing from the spirit and scope of the present invention.

This application is based on Japanese Patent Applications No. 2014-027764 filed on Feb. 17, 2014, the contents of which are incorporated herein by reference.

The invention claimed is:

1. A method for producing a carbonate compound and methacrylic acid or an ester thereof, comprising:
(a1) a step of reacting acetone with chlorine molecule to obtain hexachloroacetone and hydrogen chloride,
(a2) a step of reacting the hexachloroacetone obtained in the step (a1) with an alkyl alcohol having a carbon number of from 1 to 10 to obtain a dialkyl carbonate and chloroform,
(b1) a step of reacting chloroform with acetone to obtain 1,1,1-trichloro-2-methyl-2-propanol,
(b2) a step of reacting the 1,1,1-trichloro-2-methyl-2-propanol obtained in the step (b1) with water or an alcohol that has a carbon number of from 1 to 10 in which a part or all of hydrogen atoms bonded to carbon atoms may be replaced by halogen atom(s) and/or deuterium atom(s), to obtain 2-chloro-2-methylpropanoic acid or an ester thereof and hydrogen chloride,
(b3) a step of obtaining methacrylic acid or an ester thereof and hydrogen chloride from the 2-chloro-2-methylpropanoic acid or the ester thereof obtained in the step (b2), and
(c1) a step of reacting the hydrogen chloride obtained in the step (a1), the step (b2), and the step (b3) with oxygen molecule to obtain chlorine molecule,
wherein the step (b2) contains reacting the 1,1,1-trichloro-2-methyl-2-propanol obtained in the step (b1) in the presence of a Lewis acid catalyst at a temperature lower than the boiling point of the 1,1,1-trichloro-2-methyl-2-propanol,
after the chloroform is obtained in the step (a2), the chloroform obtained in the step (a2) is used as at least a part of the chloroform in the step (b1), and
after the chlorine molecule is obtained in the step (c1), the chlorine molecule obtained in the step (c1) is used as at least a part of the chlorine molecule in the step (a1).

2. The method for producing a carbonate compound and methacrylic acid or an ester thereof according to claim 1,
wherein the step (b2) comprises reacting the 1,1,1-trichloro-2-methyl-2-propanol obtained in the step (b1) in the presence of the Lewis acid catalyst at the temperature lower than the boiling point of the 1,1,1-trichloro-2-methyl-2-propanol and further reacting the resulting one with the water or the alcohol that has a carbon number of from 1 to 10 in which a part or all of hydrogen atoms bonded to carbon atoms may be replaced by halogen atom(s) and/or deuterium atom(s), to obtain the 2-chloro-2-methylpropanoic acid or the ester thereof and the hydrogen chloride.

3. The method for producing a carbonate compound and methacrylic acid or an ester thereof according to claim 1,
wherein the step (b2) comprises reacting the 1,1,1-trichloro-2-methyl-2-propanol obtained in the step (b1) with the water or the alcohol that has a carbon number of from 1 to 10 in which a part or all of hydrogen atoms bonded to carbon atoms may be replaced by halogen atom(s) and/or deuterium atom(s), in the presence of the Lewis acid catalyst at the temperature lower than the boiling point of the 1,1,1-trichloro-2-methyl-2-propanol to obtain the 2-chloro-2-methylpropanoic acid or the ester thereof and the hydrogen chloride.

4. A method for producing a carbonate compound and methacrylic acid or an ester thereof, comprising:
(a1) a step of reacting acetone with chlorine molecule to obtain hexachloroacetone and hydrogen chloride,
(a2) a step of reacting the hexachloroacetone obtained in the step (a1) with an alkyl alcohol having a carbon number of from 1 to 10 to obtain a dialkyl carbonate and chloroform,
(b1) a step of reacting chloroform with acetone to obtain 1,1,1-trichloro-2-methyl-2-propanol,
(b4) a step of reacting the 1,1,1-trichloro-2-methyl-2-propanol obtained in the step (b1) with water or an alcohol that has a carbon number of from 1 to 10 in which a part or all of hydrogen atoms bonded to carbon atoms may be replaced by halogen atom(s) and/or deuterium atom(s), in the presence of a Lewis acid catalyst at a temperature equal to or higher than the boiling point of the 1,1,1-trichloro-2-methyl-2-propanol to obtain methacrylic acid or an ester thereof and hydrogen chloride, and
(c2) a step of reacting the hydrogen chloride obtained in the step (a1) and the step (b4) with oxygen molecule to obtain chlorine molecule,
wherein, after the chloroform is obtained in the step (a2), the chloroform obtained in the step (a2) is used as at least a part of the chloroform in the step (b1), and
after the chlorine molecule is obtained in the step (c2), the chlorine molecule obtained in the step (c2) is used as at least a part of the chlorine molecule in the step (a1).

5. The method for producing a carbonate compound and methacrylic acid or an ester thereof according to claim 1, further comprising:
(a3) a step of reacting the dialkyl carbonate obtained in the step (a2) with phenol to obtain diphenyl carbonate and an alkyl alcohol having a carbon number of from 1 to 10, and
(a4) a step of reacting the diphenyl carbonate obtained in the step (a3) with bisphenol A to obtain an aromatic polycarbonate and phenol
wherein, after the alkyl alcohol having a carbon number of from 1 to 10 is obtained in the step (a3), the alkyl alcohol having a carbon number of from 1 to 10 obtained in the step (a3) is used as at least a part of the alkyl alcohol having a carbon number of from 1 to 10 in the step (a2), and
after the phenol is obtained in the step (a4), the phenol obtained in the step (a4) is used as at least a part of the phenol in the step (a3).

6. The method for producing a carbonate compound and methacrylic acid or an ester thereof according to claim 2, further comprising:
(a3) a step of reacting the dialkyl carbonate obtained in the step (a2) with phenol to obtain diphenyl carbonate and an alkyl alcohol having a carbon number of from 1 to 10, and
(a4) a step of reacting the diphenyl carbonate obtained in the step (a3) with bisphenol A to obtain an aromatic polycarbonate and phenol
wherein, after the alkyl alcohol having a carbon number of from 1 to 10 is obtained in the step (a3), the alkyl alcohol having a carbon number of from 1 to 10 obtained in the step (a3) is used as at least a part of the alkyl alcohol having a carbon number of from 1 to 10 in the step (a2), and
after the phenol is obtained in the step (a4), the phenol obtained in the step (a4) is used as at least a part of the phenol in the step (a3).

7. The method for producing a carbonate compound and methacrylic acid or an ester thereof according to claim 3, further comprising:

(a3) a step of reacting the dialkyl carbonate obtained in the step (a2) with phenol to obtain diphenyl carbonate and an alkyl alcohol having a carbon number of from 1 to 10, and (a4) a step of reacting the diphenyl carbonate obtained in the step (a3) with bisphenol A to obtain an aromatic polycarbonate and phenol wherein, after the alkyl alcohol having a carbon number of from 1 to 10 is obtained in the step (a3), the alkyl alcohol having a carbon number of from 1 to 10 obtained in the step (a3) is used as at least a part of the alkyl alcohol having a carbon number of from 1 to 10 in the step (a2), and after the phenol is obtained in the step (a4), the phenol obtained in the step (a4) is used as at least a part of the phenol in the step (a3).

8. The method for producing a carbonate compound and methacrylic acid or an ester thereof according to claim 4, further comprising:

(a3) a step of reacting the dialkyl carbonate obtained in the step (a2) with phenol to obtain diphenyl carbonate and an alkyl alcohol having a carbon number of from 1 to 10, and (a4) a step of reacting the diphenyl carbonate obtained in the step (a3) with bisphenol A to obtain an aromatic polycarbonate and phenol wherein, after the alkyl alcohol having a carbon number of from 1 to 10 is obtained in the step (a3), the alkyl alcohol having a carbon number of from 1 to 10 obtained in the step (a3) is used as at least a part of the alkyl alcohol having a carbon number of from 1 to 10 in the step (a2), and after the phenol is obtained in the step (a4), the phenol obtained in the step (a4) is used as at least a part of the phenol in the step (a3).

\* \* \* \* \*